United States Patent
Padmani et al.

(10) Patent No.: US 12,412,644 B2
(45) Date of Patent: Sep. 9, 2025

(54) AUTOMATED EXCHANGE OF HEALTHCARE INFORMATION FOR FULFILLMENT OF MEDICATION DOSES

(71) Applicant: Baxter Corporation Englewood, Englewood, CO (US)

(72) Inventors: Bhavesh S. Padmani, Port Orange, FL (US); Gregory T. Olsen, Deland, FL (US); Ghalib A. Abbasi, Ormond Beach, FL (US); Cherie Dooley, Englewood, CO (US); Douglas Leech, Aurora, CO (US); Cory D. Armstrong, Englewood, CO (US); Russell White, Englewood, CO (US)

(73) Assignee: Baxter Corporation Englewood, Englewood, CO (US)

( * ) Notice: Subject to any disclaimer, the term of this patent is extended or adjusted under 35 U.S.C. 154(b) by 1020 days.

(21) Appl. No.: 14/922,376

(22) Filed: Oct. 26, 2015

(65) Prior Publication Data

US 2016/0117472 A1 Apr. 28, 2016

Related U.S. Application Data

(60) Provisional application No. 62/068,301, filed on Oct. 24, 2014.

(51) Int. Cl.
| | |
|---|---|
| *G16H 10/60* | (2018.01) |
| *G16H 20/10* | (2018.01) |
| *G16H 70/40* | (2018.01) |

(52) U.S. Cl.
CPC ............ *G16H 10/60* (2018.01); *G16H 20/10* (2018.01); *G16H 70/40* (2018.01)

(58) Field of Classification Search
CPC ... G06F 19/3456; G06F 19/326; G16H 20/10; G16H 10/60; G16H 70/40
See application file for complete search history.

(56) References Cited

U.S. PATENT DOCUMENTS

| | | |
|---|---|---|
| 641,748 A | 1/1900 | Smith |
| 819,339 A | 5/1906 | Cleland |

(Continued)

FOREIGN PATENT DOCUMENTS

| | | |
|---|---|---|
| CN | 1516257 | 5/1999 |
| CN | 2440518 | 8/2001 |

(Continued)

OTHER PUBLICATIONS

Texas Administrative Code, Title 22, Part 15, Ch 291, Rules 20, 36, and 71-74. Feb. 10, 2004.

(Continued)

*Primary Examiner* — Chad A Newton
(74) *Attorney, Agent, or Firm* — K&L Gates LLP

(57) ABSTRACT

Automated healthcare information exchange. The healthcare information may comprise one or more dose orders corresponding to dose medications to be administered to a patient. The healthcare information may be received (e.g., from an EMR system such as a hospital information system (HIS) or the like) in the form of a healthcare information data stream. The information may then be standardized in to a standardized intermediate form. For instance, data may be parsed from the data stream and used to populate a staging table. In turn, data from the staging table may be transformed into an input format specific to a given dose fulfillment client to which the dose order is provided for fulfillment of the dose. Additionally, exception processing, logistical processing, and management functionality may be applied to the dose orders.

25 Claims, 18 Drawing Sheets

(56) References Cited

U.S. PATENT DOCUMENTS

| | | |
|---|---|---|
| 3,426,150 A | 2/1969 | Tygart |
| 3,739,943 A | 6/1973 | Williamsen et al. |
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,878,967 A | 4/1975 | Joslin et al. |
| 3,910,257 A | 10/1975 | Fletcher et al. |
| 3,910,260 A | 10/1975 | Sarnoff et al. |
| 3,921,196 A | 11/1975 | Patterson |
| 3,971,000 A | 7/1976 | Cromwell |
| 3,995,630 A | 12/1976 | Verrdonk |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,414,566 A | 11/1983 | Peyton et al. |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,526,574 A | 7/1985 | Pekkarinen |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,564,054 A | 1/1986 | Gustavsson |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,653,010 A | 3/1987 | Figler et al. |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| D293,135 S | 12/1987 | Medema et al. |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,770,184 A | 9/1988 | Greene et al. |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,829,524 A | 5/1989 | Yoshida |
| 4,830,018 A | 5/1989 | Treach |
| 4,831,562 A | 5/1989 | Mcintosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,880,013 A | 11/1989 | Chio |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,905,163 A | 2/1990 | Garber et al. |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |

(56) References Cited

U.S. PATENT DOCUMENTS

| | | |
|---|---|---|
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,943,987 A | 7/1990 | Asahina et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,964,847 A | 10/1990 | Prince |
| 4,966,579 A | 10/1990 | Polaschegg |
| 4,967,928 A | 11/1990 | Carter |
| 4,968,295 A | 11/1990 | Neumann |
| 4,975,647 A | 12/1990 | Downer et al. |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,103,211 A | 4/1992 | Daoud et al. |
| 5,104,374 A | 4/1992 | Bishko et al. |
| 5,108,131 A | 4/1992 | Nassim |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,884 A | 11/1993 | Stern et al. |
| 5,262,943 A | 11/1993 | Thibado et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,324,422 A | 6/1994 | Colleran et al. |
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |
| 5,337,230 A | 8/1994 | Baumgartner et al. |
| 5,337,747 A | 8/1994 | Neftel |
| 5,337,919 A | 8/1994 | Spaulding et al. |
| 5,338,157 A | 8/1994 | Blomquist |
| 5,339,421 A | 8/1994 | Housel, III |
| 5,339,821 A | 8/1994 | Fujimoto |
| 5,341,291 A | 8/1994 | Roizen et al. |
| 5,341,412 A | 8/1994 | Ramot et al. |
| 5,348,008 A | 9/1994 | Bornn et al. |

(56) References Cited

U.S. PATENT DOCUMENTS

| | | |
|---|---|---|
| 5,348,539 A | 9/1994 | Herskowitz |
| 5,349,675 A | 9/1994 | Fitzgerald et al. |
| 5,356,378 A | 10/1994 | Doan |
| 5,360,410 A | 11/1994 | Wacks |
| 5,361,202 A | 11/1994 | Doue |
| 5,361,758 A | 11/1994 | Hall et al. |
| 5,366,896 A | 11/1994 | Margrey et al. |
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,201 A | 7/1995 | Torchia et al. |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson et al. |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,318 A | 4/1996 | Gomes |
| 5,509,422 A | 4/1996 | Fukami |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,434 A | 10/1996 | Halperin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | Mcilroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,591,344 A | 1/1997 | Kenley et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |

(56) References Cited

U.S. PATENT DOCUMENTS

| | | |
|---|---|---|
| 5,641,628 A | 6/1997 | Bianchi |
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,788,851 A | 8/1998 | Kenley et al. |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |
| 5,835,897 A | 11/1998 | Dang |
| 5,836,910 A | 11/1998 | Duffy et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zimi et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,907,493 A | 5/1999 | Boyer et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toavs et al. |
| 5,921,938 A | 7/1999 | Aoyama et al. |
| 5,923,018 A | 7/1999 | Kameda et al. |

(56) References Cited

U.S. PATENT DOCUMENTS

| | | |
|---|---|---|
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,941,846 A | 8/1999 | Duffy et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| D414,578 S | 9/1999 | Chen et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,961,923 A | 10/1999 | Nova et al. |
| 5,963,641 A | 10/1999 | Crandall et al. |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,939 A | 11/1999 | Berman et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DeRienzo |
| 6,006,946 A | 12/1999 | Williams et al. |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,048,086 A | 4/2000 | Valerino |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,068,156 A | 5/2000 | Liff et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,081,786 A | 6/2000 | Barry et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,096,561 A | 8/2000 | Tayi |
| 6,098,892 A | 8/2000 | Peoples, Jr. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,177 A | 10/2000 | Venkatraman et al. |
| 6,139,495 A | 10/2000 | De La Huerga |
| 6,141,412 A | 10/2000 | Smith et al. |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,161,141 A | 12/2000 | Dillon |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |

(56) References Cited

U.S. PATENT DOCUMENTS

| | | |
|---|---|---|
| 6,176,392 B1 | 1/2001 | William et al. |
| 6,182,047 B1 | 1/2001 | Dirbas |
| 6,183,417 B1 | 2/2001 | Geheb et al. |
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,202,923 B1 | 3/2001 | Boyer et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,213,972 B1 | 4/2001 | Butterfield et al. |
| 6,219,439 B1 | 4/2001 | Burger |
| 6,219,587 B1 | 4/2001 | Ahlin et al. |
| 6,221,009 B1 | 4/2001 | Doi et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,226,745 B1 | 5/2001 | Wiederhold |
| 6,230,142 B1 | 5/2001 | Benigno et al. |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,260,021 B1 | 7/2001 | Wong et al. |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,278,999 B1 | 8/2001 | Knapp |
| 6,283,322 B1 | 9/2001 | Liff et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,502 B1 | 11/2001 | Schoenberg et al. |
| 6,322,504 B1 | 11/2001 | Kirshner |
| 6,322,515 B1 | 11/2001 | Goor et al. |
| 6,330,491 B1 | 12/2001 | Lion |
| 6,332,090 B1 | 12/2001 | DeFrank et al. |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,347,553 B1 | 2/2002 | Morris et al. |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,401,072 B1 | 6/2002 | Haudenschild et al. |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |
| 6,421,650 B1 | 7/2002 | Goetz et al. |
| 6,424,996 B1 | 7/2002 | Killcommons et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,438,451 B1 | 8/2002 | Lion |
| RE37,829 E | 9/2002 | Charhut et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,461,037 B1 | 10/2002 | O'Leary |
| 6,463,310 B1 | 10/2002 | Swedlow et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,471,646 B1 | 10/2002 | Thede |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,494,831 B1 | 12/2002 | Koritzinsky |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,564,121 B1 | 5/2003 | Wallace et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,581,798 B2 | 6/2003 | Liff et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |

(56) References Cited

U.S. PATENT DOCUMENTS

| | | |
|---|---|---|
| 6,602,469 B1 | 8/2003 | Maus et al. |
| 6,607,485 B2 | 8/2003 | Bardy |
| 6,610,973 B1 | 8/2003 | Davis, III |
| 6,613,009 B1 | 9/2003 | Bainbridge et al. |
| 6,616,633 B1 | 9/2003 | Butterfield et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,669,663 B1 | 12/2003 | Thompson |
| 6,673,314 B1 | 1/2004 | Burbank et al. |
| 6,687,546 B2 | 2/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,711,460 B1 | 3/2004 | Reese |
| 6,731,324 B2 | 5/2004 | Levy |
| 6,733,447 B2 | 5/2004 | Lai et al. |
| 6,735,497 B2 | 5/2004 | Wallace et al. |
| 6,740,075 B2 | 5/2004 | Lebel et al. |
| 6,746,398 B2 | 6/2004 | Hervy et al. |
| 6,758,810 B2 | 7/2004 | Lebel et al. |
| 6,768,425 B2 | 7/2004 | Flaherty et al. |
| 6,771,369 B2 | 8/2004 | Rzasa et al. |
| 6,775,602 B2 | 8/2004 | Gordon, Jr. et al. |
| 6,776,304 B2 | 8/2004 | Liff et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,473 B1 | 11/2004 | Bruker |
| 6,813,519 B2 | 11/2004 | Lebel et al. |
| 6,814,255 B2 | 11/2004 | Liff et al. |
| 6,820,093 B2 | 11/2004 | De La Huerga |
| 6,842,736 B1 | 1/2005 | Brzozowski |
| 6,847,861 B2 | 1/2005 | Lunak et al. |
| 6,854,088 B2 | 2/2005 | Massengale et al. |
| 6,871,211 B2 | 3/2005 | Labounty et al. |
| 6,873,268 B2 | 3/2005 | Lebel et al. |
| 6,877,530 B2 | 4/2005 | Osborne et al. |
| 6,880,034 B2 | 4/2005 | Manke et al. |
| 6,885,288 B2 | 4/2005 | Pincus |
| 6,887,201 B2 | 5/2005 | Bardy |
| 6,892,941 B2 | 5/2005 | Rosenblum |
| 6,912,549 B2 | 6/2005 | Rotter et al. |
| 6,913,590 B2 | 7/2005 | Sorenson et al. |
| 6,915,265 B1 | 7/2005 | Johnson |
| 6,915,823 B2 | 7/2005 | Osborne et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,975,924 B2 | 12/2005 | Kircher et al. |
| 6,976,628 B2 | 12/2005 | Krupa |
| 6,979,306 B2 | 12/2005 | Moll |
| 6,980,958 B1 | 12/2005 | Surwit et al. |
| 6,981,644 B2 | 1/2006 | Cheong et al. |
| 6,985,870 B2 | 1/2006 | Martucci et al. |
| 6,991,002 B2 | 1/2006 | Osborne et al. |
| 6,995,664 B1 | 2/2006 | Darling |
| 7,006,893 B2 | 2/2006 | Hart et al. |
| 7,015,806 B2 | 3/2006 | Naidoo et al. |
| 7,017,622 B2 | 3/2006 | Osborne et al. |
| 7,017,623 B2 | 3/2006 | Tribble et al. |
| 7,028,723 B1 | 4/2006 | Alouani et al. |
| 7,096,212 B2 | 8/2006 | Tribble et al. |
| 7,117,902 B2 | 10/2006 | Osborne |
| 7,151,982 B2 | 12/2006 | Liff et al. |
| 7,194,336 B2 | 3/2007 | DiGianfilippo et al. |
| 7,209,891 B1 | 4/2007 | Addy et al. |
| 7,240,699 B2 | 7/2007 | Osborne et al. |
| 7,255,680 B1 | 8/2007 | Gharib |
| 7,277,579 B2 | 10/2007 | Huang |
| 7,277,757 B2 | 10/2007 | Casavant et al. |
| 7,317,967 B2 | 1/2008 | DiGianfilippo et al. |
| 7,321,861 B1 | 1/2008 | Oon |
| 7,343,224 B2 | 3/2008 | DiGianfilippo et al. |
| 7,403,901 B1 | 7/2008 | Carley et al. |
| 7,427,002 B2 | 9/2008 | Liff et al. |
| 7,493,263 B2 | 2/2009 | Helmus et al. |
| 7,499,581 B2 | 3/2009 | Tribble et al. |
| 7,509,280 B1 | 3/2009 | Haudenschild |
| 7,555,557 B2 | 6/2009 | Bradley et al. |
| 7,561,312 B1 | 7/2009 | Proudfoot et al. |
| 7,581,953 B2 | 9/2009 | Lehmann et al. |
| 7,599,516 B2 | 10/2009 | Limer et al. |
| 7,610,115 B2 | 10/2009 | Rob et al. |
| 7,630,908 B1 | 12/2009 | Amrien et al. |
| 7,636,718 B1 | 12/2009 | Steen et al. |
| 7,672,859 B1 | 3/2010 | Louie et al. |
| 7,698,019 B2 | 4/2010 | Moncrief et al. |
| 7,698,154 B2 | 4/2010 | Marchosky |
| 7,734,478 B2 | 6/2010 | Goodall et al. |
| 7,753,085 B2 | 7/2010 | Tribble et al. |
| 7,769,601 B1 | 8/2010 | Bleser et al. |
| 7,783,383 B2 | 8/2010 | Eliuk et al. |
| D624,225 S | 9/2010 | Federico et al. |
| 7,801,642 B2 | 9/2010 | Ansari et al. |
| 7,847,970 B1 | 12/2010 | McGrady |
| 7,853,621 B2 | 12/2010 | Guo |
| 7,904,822 B2 | 3/2011 | Monteleone et al. |
| 7,931,859 B2 | 4/2011 | Mlodzinski et al. |
| 7,937,290 B2 | 5/2011 | Bahir |
| 7,986,369 B1 | 7/2011 | Burns |
| 7,991,507 B2 | 8/2011 | Liff et al. |
| 8,170,271 B2 | 5/2012 | Chen |
| 8,191,339 B2 | 6/2012 | Tribble et al. |
| 8,215,557 B1 | 7/2012 | Reno et al. |
| 8,220,503 B2 | 7/2012 | Tribble et al. |
| 8,225,824 B2 | 7/2012 | Eliuk et al. |
| D667,961 S | 9/2012 | Marmier |
| 8,267,129 B2 | 9/2012 | Doherty et al. |
| 8,271,138 B2 | 9/2012 | Eliuk et al. |
| 8,280,549 B2 | 10/2012 | Liff et al. |
| 8,284,305 B2 | 10/2012 | Newcomb et al. |
| 8,374,887 B1 | 2/2013 | Alexander |
| 8,386,070 B2 | 2/2013 | Eliuk et al. |
| 8,548,824 B1 | 10/2013 | daCosta |
| 8,554,579 B2 | 10/2013 | Tribble et al. |
| D693,480 S | 11/2013 | Spiess et al. |
| 8,595,206 B1 | 11/2013 | Ansari et al. |
| 8,666,541 B1 | 3/2014 | Ansari et al. |
| 8,678,047 B2 | 3/2014 | Tribble et al. |
| D715,958 S | 10/2014 | Bossart et al. |
| 9,053,218 B2 | 6/2015 | Osborne et al. |
| D733,480 S | 7/2015 | Shao |
| D738,152 S | 9/2015 | Grasselli et al. |
| D753,428 S | 4/2016 | Shao |
| 9,362,969 B1 | 6/2016 | Burgess et al. |
| 9,382,021 B2 | 7/2016 | Tribble et al. |
| 9,662,273 B2 | 5/2017 | Ranalletta et al. |
| 9,930,297 B2 | 3/2018 | Alexander et al. |
| 9,956,145 B2 | 5/2018 | Thompson et al. |
| 2001/0001237 A1 | 5/2001 | Stroda et al. |
| 2001/0003177 A1 | 6/2001 | Schena et al. |
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0025138 A1 | 9/2001 | Bardy |
| 2001/0025156 A1 | 9/2001 | Bui et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034614 A1 | 10/2001 | Fletcher-Haynes et al. |
| 2001/0034616 A1 | 10/2001 | Giannini |

(56) References Cited

U.S. PATENT DOCUMENTS

| | | |
|---|---|---|
| 2001/0037057 A1 | 11/2001 | Bardy |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041920 A1 | 11/2001 | Starkweather et al. |
| 2001/0044588 A1 | 11/2001 | Mault |
| 2001/0044731 A1 | 11/2001 | Coffman et al. |
| 2001/0047125 A1 | 11/2001 | Quy |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0007285 A1 | 1/2002 | Rappaport |
| 2002/0010568 A1 | 1/2002 | Rubbert et al. |
| 2002/0010679 A1 | 1/2002 | Felsher |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032582 A1 | 3/2002 | Feeney et al. |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0062227 A1 | 5/2002 | Yuyama |
| 2002/0062229 A1 | 5/2002 | Alban et al. |
| 2002/0065540 A1 | 5/2002 | Lebel et al. |
| 2002/0065686 A1 | 5/2002 | Monteleone et al. |
| 2002/0067273 A1 | 6/2002 | Jaques et al. |
| 2002/0072733 A1 | 6/2002 | Flaherty |
| 2002/0073250 A1 | 6/2002 | Ommering |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0091309 A1 | 7/2002 | Auer |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116226 A1 | 8/2002 | Auer et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiuro |
| 2002/0165491 A1 | 11/2002 | Reilly |
| 2002/0169636 A1 | 11/2002 | Eggers et al. |
| 2002/0173875 A1 | 11/2002 | Wallace et al. |
| 2002/0188467 A1 | 12/2002 | Eke |
| 2002/0198473 A1 | 12/2002 | Kumar et al. |
| 2002/0198513 A1 | 12/2002 | Lebel et al. |
| 2002/0198624 A1 | 12/2002 | Greenwald |
| 2003/0006878 A1 | 1/2003 | Chung |
| 2003/0023177 A1 | 1/2003 | Bardy |
| 2003/0033532 A1 | 2/2003 | Marks |
| 2003/0036783 A1 | 2/2003 | Bauhahn et al. |
| 2003/0046114 A1 | 3/2003 | Davies et al. |
| 2003/0046280 A1 | 3/2003 | Rotter et al. |
| 2003/0046439 A1 | 3/2003 | Manke et al. |
| 2003/0050621 A1 | 3/2003 | Lebel et al. |
| 2003/0050731 A1 | 3/2003 | Rosenblum |
| 2003/0052787 A1 | 3/2003 | Zerhusen |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0065287 A1 | 4/2003 | Spohn et al. |
| 2003/0076736 A1 | 4/2003 | Buker et al. |
| 2003/0078534 A1 | 4/2003 | Hochman et al. |
| 2003/0079746 A1 | 5/2003 | Hickle |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0097368 A1* | 5/2003 | Tribble ............... G06F 19/3456 |
| 2003/0114836 A1 | 6/2003 | Estes et al. |
| 2003/0117580 A1 | 6/2003 | Franz et al. |
| 2003/0125609 A1 | 7/2003 | Becker |
| 2003/0125611 A1 | 7/2003 | Bardy |
| 2003/0139701 A1 | 7/2003 | White et al. |
| 2003/0144878 A1 | 7/2003 | Wilkes et al. |
| 2003/0149599 A1 | 8/2003 | Goodall et al. |
| 2003/0154108 A1 | 8/2003 | Fletcher-Haynes et al. |
| 2003/0158508 A1 | 8/2003 | DiGianfilippo |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0179287 A1 | 9/2003 | Kozic et al. |
| 2003/0181851 A1 | 9/2003 | Mann et al. |
| 2003/0182164 A1 | 9/2003 | Blomquist |
| 2003/0195397 A1 | 10/2003 | Bardy |
| 2003/0200117 A1 | 10/2003 | Manetta et al. |
| 2003/0201697 A1 | 10/2003 | Richardson |
| 2003/0212379 A1 | 11/2003 | Bylund et al. |
| 2003/0225596 A1 | 12/2003 | Richardson et al. |
| 2003/0225728 A1 | 12/2003 | Moura |
| 2003/0231803 A1 | 12/2003 | Huang |
| 2004/0002874 A1 | 1/2004 | Shaffer et al. |
| 2004/0017475 A1 | 1/2004 | Akers et al. |
| 2004/0019607 A1 | 1/2004 | Moubayed et al. |
| 2004/0039260 A1 | 2/2004 | Bardy |
| 2004/0039264 A1 | 2/2004 | Bardy |
| 2004/0051368 A1 | 3/2004 | Caputo et al. |
| 2004/0055611 A1 | 3/2004 | Penny et al. |
| 2004/0064343 A1 | 4/2004 | Korpman et al. |
| 2004/0073329 A1 | 4/2004 | Engleson |
| 2004/0088187 A1 | 5/2004 | Chudy et al. |
| 2004/0088374 A1 | 5/2004 | Webb et al. |
| 2004/0111293 A1 | 6/2004 | Firanek et al. |
| 2004/0115132 A1 | 6/2004 | Young et al. |
| 2004/0116862 A1 | 6/2004 | Ray |
| 2004/0117215 A1 | 6/2004 | Marchosky |
| 2004/0128162 A1 | 7/2004 | Schlotterbeck et al. |
| 2004/0129616 A1 | 7/2004 | Mori et al. |
| 2004/0148195 A1 | 7/2004 | Kalies |
| 2004/0158193 A1 | 8/2004 | Bui et al. |
| 2004/0172283 A1 | 9/2004 | Vanderveen et al. |
| 2004/0172289 A1 | 9/2004 | Kozic et al. |
| 2004/0172300 A1 | 9/2004 | Mihai et al. |
| 2004/0193328 A1 | 9/2004 | Zaitsu et al. |
| 2004/0193453 A1 | 9/2004 | Butterfield et al. |
| 2004/0204673 A1 | 10/2004 | Flaherty |
| 2004/0204954 A1 | 10/2004 | Lacko |
| 2004/0215490 A1 | 10/2004 | Duchon et al. |
| 2004/0220829 A1 | 11/2004 | Baharav et al. |
| 2004/0225528 A1 | 11/2004 | Brock |
| 2004/0235446 A1 | 11/2004 | Flaherty et al. |
| 2004/0236630 A1 | 11/2004 | Kost et al. |

(56) References Cited

U.S. PATENT DOCUMENTS

| | | |
|---|---|---|
| 2004/0248295 A1 | 12/2004 | Katsuhiko et al. |
| 2004/0260233 A1 | 12/2004 | Garibotto et al. |
| 2004/0260577 A1 | 12/2004 | Dahlin et al. |
| 2005/0001033 A1 | 1/2005 | Cheong et al. |
| 2005/0017864 A1 | 1/2005 | Tsoukalis |
| 2005/0033124 A1 | 2/2005 | Kelly et al. |
| 2005/0033773 A1 | 2/2005 | Roberge et al. |
| 2005/0038680 A1 | 2/2005 | McMahon |
| 2005/0039742 A1 | 2/2005 | Hickle |
| 2005/0043665 A1 | 2/2005 | Vinci et al. |
| 2005/0045548 A1 | 3/2005 | Brugger et al. |
| 2005/0054923 A1 | 3/2005 | Pan |
| 2005/0060372 A1 | 3/2005 | DeBettencourt et al. |
| 2005/0080651 A1 | 4/2005 | Morrison et al. |
| 2005/0187794 A1 | 8/2005 | Kimak |
| 2005/0209737 A1 | 9/2005 | Kircher |
| 2005/0228238 A1 | 10/2005 | Monitzer |
| 2005/0279419 A1 | 12/2005 | Tribble et al. |
| 2006/0084042 A1 | 4/2006 | Weaver et al. |
| 2006/0124656 A1 | 6/2006 | Popovic, Jr. |
| 2006/0136095 A1 | 6/2006 | Rob et al. |
| 2006/0149416 A1* | 7/2006 | Mohapatra .............. G16H 20/10 700/242 |
| 2006/0161294 A1 | 7/2006 | DiMaggio |
| 2006/0173714 A1 | 8/2006 | Grotzinger |
| 2006/0178578 A1 | 8/2006 | Tribble et al. |
| 2006/0181391 A1 | 8/2006 | McNeill et al. |
| 2006/0235881 A1 | 10/2006 | Masarie et al. |
| 2007/0038915 A1* | 2/2007 | Alaimo ................ G11B 20/182 |
| 2007/0043767 A1 | 2/2007 | Osborne et al. |
| 2007/0047980 A1 | 3/2007 | Limer et al. |
| 2007/0088568 A1 | 4/2007 | Goodall et al. |
| 2007/0110305 A1 | 5/2007 | Corcoran et al. |
| 2007/0125442 A1 | 6/2007 | Tribble et al. |
| 2007/0168228 A1* | 7/2007 | Lawless .............. G06F 19/3418 705/2 |
| 2007/0179806 A1 | 8/2007 | Knowlton et al. |
| 2007/0189597 A1 | 8/2007 | Limer et al. |
| 2007/0192139 A1 | 8/2007 | Cookson et al. |
| 2007/0216998 A1 | 9/2007 | Sander |
| 2007/0239482 A1 | 10/2007 | Finn et al. |
| 2007/0239997 A1 | 10/2007 | Qu et al. |
| 2008/0046292 A1 | 2/2008 | Myers et al. |
| 2008/0056556 A1 | 3/2008 | Eller et al. |
| 2008/0059228 A1 | 3/2008 | Bossi et al. |
| 2008/0091467 A1 | 4/2008 | Moncrief et al. |
| 2008/0119958 A1 | 5/2008 | Bear et al. |
| 2008/0125897 A1 | 5/2008 | DiGianfilippo et al. |
| 2008/0147554 A1 | 6/2008 | Stevens et al. |
| 2008/0195246 A1 | 8/2008 | Tribble et al. |
| 2008/0306926 A1 | 12/2008 | Friedlander et al. |
| 2009/0024414 A1 | 1/2009 | Mansour et al. |
| 2009/0080408 A1 | 3/2009 | Natoli et al. |
| 2009/0097368 A1 | 4/2009 | Vlutters et al. |
| 2009/0138340 A1 | 5/2009 | Borr et al. |
| 2009/0188937 A1 | 7/2009 | Kim |
| 2009/0205877 A1 | 8/2009 | Claypool |
| 2009/0210252 A1 | 8/2009 | Silver |
| 2009/0235194 A1 | 9/2009 | Arndt et al. |
| 2009/0258331 A1 | 10/2009 | Do et al. |
| 2009/0285762 A1 | 11/2009 | Flower |
| 2009/0313044 A1 | 12/2009 | Haque et al. |
| 2009/0323170 A1 | 12/2009 | Lin |
| 2009/0324032 A1 | 12/2009 | Chen |
| 2010/0010841 A1* | 1/2010 | Cooper ................ G06Q 10/02 705/6 |
| 2010/0017031 A1 | 1/2010 | Rob et al. |
| 2010/0091281 A1 | 4/2010 | Suzuki |
| 2010/0094653 A1 | 4/2010 | Tribble et al. |
| 2010/0128165 A1 | 5/2010 | Newcomb et al. |
| 2010/0157293 A9 | 6/2010 | Rzasa et al. |
| 2010/0185456 A1 | 7/2010 | Kansal |
| 2010/0241270 A1 | 9/2010 | Eliuk et al. |
| 2011/0119088 A1* | 5/2011 | Gunn ................ G06Q 50/24 705/3 |
| 2011/0191121 A1 | 8/2011 | Fioravanti |
| 2011/0202366 A1 | 8/2011 | Akers et al. |
| 2011/0208350 A1 | 8/2011 | Eliuk et al. |
| 2011/0267465 A1 | 11/2011 | Alexander et al. |
| 2012/0097290 A1 | 4/2012 | Mikhaeil |
| 2012/0200596 A1 | 8/2012 | Gotou et al. |
| 2012/0211565 A1 | 8/2012 | Colavito et al. |
| 2012/0303388 A1 | 11/2012 | Vishnubhalta et al. |
| 2013/0079581 A1 | 3/2013 | Agamaite et al. |
| 2013/0090947 A1 | 4/2013 | Nockley |
| 2013/0197445 A1 | 8/2013 | Schabbach et al. |
| 2013/0262138 A1 | 10/2013 | Jaskela et al. |
| 2013/0279774 A1 | 10/2013 | Helgason et al. |
| 2013/0304510 A1 | 11/2013 | Chan et al. |
| 2013/0314535 A1 | 11/2013 | Yuyama et al. |
| 2013/0342676 A1 | 12/2013 | Amano |
| 2014/0022569 A1 | 1/2014 | Matsui et al. |
| 2014/0156064 A1 | 6/2014 | Crawford et al. |
| 2014/0156294 A1 | 6/2014 | Tribble et al. |
| 2014/0214436 A1 | 7/2014 | Utech et al. |
| 2014/0350950 A1 | 11/2014 | Jaskela et al. |
| 2015/0205932 A1 | 7/2015 | Tribble |
| 2015/0227719 A1 | 8/2015 | Ranalletta |
| 2015/0272320 A1* | 10/2015 | Ranalletta .............. G06V 20/66 108/23 |
| 2015/0278477 A1 | 10/2015 | Tribble |
| 2015/0286799 A1 | 10/2015 | Padmani |
| 2016/0072985 A1 | 3/2016 | Sandmann et al. |
| 2016/0092638 A1 | 3/2016 | Padmani |
| 2016/0092639 A1 | 3/2016 | Padmani |
| 2016/0140315 A1 | 5/2016 | Diaz et al. |
| 2016/0210437 A1 | 7/2016 | Padmani et al. |
| 2016/0371462 A1 | 12/2016 | Wallen |
| 2017/0372034 A1 | 12/2017 | Tribble |

FOREIGN PATENT DOCUMENTS

| | | |
|---|---|---|
| CN | 1131076 | 12/2003 |
| EP | 0237588 | 9/1987 |
| EP | 0462466 | 12/1991 |
| EP | 0505627 | 9/1992 |
| EP | 0522527 | 1/1993 |
| EP | 0439355 | 9/1994 |
| EP | 0844581 | 5/1998 |
| EP | 0960627 | 12/1999 |
| EP | 0970655 | 1/2000 |
| EP | 1072994 | 2/2001 |
| EP | 1107158 A1 | 6/2001 |
| EP | 1097671 | 2/2003 |
| GB | 994977 A | 6/1965 |
| GB | 2210713 | 2/1987 |
| GB | 2279784 | 1/1995 |
| GB | 2285135 | 6/1995 |
| GB | 2379037 | 2/2003 |
| JP | 53137644 | 12/1978 |
| JP | 61066950 | 4/1986 |
| JP | 63068133 | 3/1988 |
| JP | 2111375 | 4/1990 |
| JP | 3423055 B2 | 1/1994 |
| JP | 06327636 | 11/1994 |
| JP | 07204253 A | 8/1995 |
| JP | 104585 | 1/1998 |
| JP | 10014890 | 1/1998 |
| JP | 10079770 | 3/1998 |
| JP | 2000036032 A | 2/2000 |
| JP | 03055131 | 4/2000 |
| JP | 2002011095 | 1/2002 |
| JP | 2002092181 A | 3/2002 |
| JP | 2002520718 | 7/2002 |
| JP | 2003022322 | 1/2003 |
| JP | 2004078970 | 3/2004 |
| JP | 2004326436 | 11/2004 |
| JP | 2004404770 A | 12/2004 |
| JP | 2005252710 A | 9/2005 |
| JP | 2006033291 A | 2/2006 |
| JP | 2006334062 | 12/2006 |
| JP | 2007198934 A | 8/2007 |
| JP | 2008139201 A | 6/2008 |
| JP | 4276654 B2 | 6/2009 |

(56) References Cited

FOREIGN PATENT DOCUMENTS

| | | |
|---|---|---|
| JP | 2009265827 A | 11/2009 |
| JP | 2010056619 A | 3/2010 |
| JP | 2010170504 | 8/2010 |
| JP | 2010533927 | 10/2010 |
| JP | 2011151430 A | 8/2011 |
| JP | 2012078265 | 4/2012 |
| JP | 5342197 B2 | 11/2013 |
| JP | 5747150 B2 | 7/2015 |
| JP | 6086813 | 3/2017 |
| KR | 20000036642 | 7/2000 |
| KR | 1020000036642 | 7/2000 |
| KR | 20010094703 A | 11/2001 |
| KR | 1020010094703 | 11/2001 |
| KR | 20050054379 | 12/2003 |
| KR | 20110115927 A | 10/2011 |
| KR | 1020110115927 | 10/2011 |
| KR | 20130001500 | 1/2013 |
| WO | WO8400493 | 2/1984 |
| WO | WO9524010 A1 | 9/1995 |
| WO | WO9634291 A1 | 10/1996 |
| WO | WO9741525 | 11/1997 |
| WO | WO9814275 A1 | 4/1998 |
| WO | WO9815092 A1 | 4/1998 |
| WO | WO9824358 A1 | 6/1998 |
| WO | WO9833433 A1 | 8/1998 |
| WO | WO9859487 | 12/1998 |
| WO | WO9904043 | 1/1999 |
| WO | WO9910029 | 3/1999 |
| WO | WO9942933 | 8/1999 |
| WO | WO9944162 | 9/1999 |
| WO | WO9959472 | 11/1999 |
| WO | WO0013588 | 3/2000 |
| WO | WO0029983 | 5/2000 |
| WO | WO0043941 | 7/2000 |
| WO | WO0052437 | 9/2000 |
| WO | WO0052626 | 9/2000 |
| WO | WO0057339 | 9/2000 |
| WO | WO0060449 | 10/2000 |
| WO | WO0069331 | 11/2000 |
| WO | WO0072181 | 11/2000 |
| WO | WO0078374 | 12/2000 |
| WO | WO0101305 | 1/2001 |
| WO | WO0102979 | 1/2001 |
| WO | WO0106468 | 1/2001 |
| WO | WO0145774 | 6/2001 |
| WO | WO0217777 | 7/2002 |
| WO | WO02091276 A1 | 11/2002 |
| WO | WO03025826 A2 | 3/2003 |
| WO | WO03094073 | 11/2003 |
| WO | WO2004070557 | 8/2004 |
| WO | WO2004070994 | 8/2004 |

OTHER PUBLICATIONS

Peterson, Charles D. and Anderson, Jr., Howard C.; "The North Dakota Telepharmacy Project: Restoring and Retaining Pharmacy Services in Rural Communities" Feb. 1, 2004.

Cato Reference Manual, Support for Trial Version (Abridged), Vienna, May 2004 Jun. 1, 2004.

Seifert et al.; "The Training of a Telepharmacist: Addressing the Needs of Rural West Texas," American Journal of Pharmaceutical Education 2004; 68 (3) Article 60. Jul. 16, 2004.

Cato Reference Manual, Vienna, May 2005 May 1, 2005.

Phillips, Jon, Associate Director of Telemedicine; "Telepharmacy at Texas Tech," presented Apr. 30, 2003, published at http://www.ttuhsc.edu/telemedicine/publication.htm at least by Jun. 22, 2003 Jun. 22, 2003.

Singapore Written Opinion for related Singapore Application No. 11201703338P; report dated Apr. 18, 2018; (6 pages).

European Search Report for related European Application No. EP15852627; report dated May 4, 2018; (16 pages).

AHRQ Health Information Technology Program-Update Jun. 2005 Fact Sheet,, http://www.ahrq.gov/research/findings/factsheets/it/hitfact/index.html—3 pages.

Albert A. Cook, "An integrated nursing-pharmacy approach to a computerized medication dispensing/administration system," Hospital Pharmacy, May 1985, pp. 321-325, vol. 20, JB Lippincott Company, Philadelphia, PA.

Allan T. Pryor, "Current State of Computer-based Patient Record Systems," Aspects of the Computer-based Patient Record, 1992, pp. 67-82, Springer-Verlag, New York, NY.

Anderson, Howard "A Narrative on the History of the Development of Telepharmacy in North Dakota from the Board of Pharmacy's Perspective Recorded by Excerpts from Board Minutes", Feb. 2006.

Angaran, "Telemedicine and telepharmacy: Current status and future implications", Am J Health-Syst Pharm, vol. 56, Jul. 15, 1999, pp. 1404-1405.

Ann Slone Endo, "Using Computers in Newborn Intensive Care Settings," American Journal of Nursing, Jul. 1981, pp. 1336-1337.

Anonymous, "Chains covet customized pharmacy integration" Drug Store New, Aug. 18, 2003, vol. 25, No. 10—p. 73.

Automated Dispensing Technologies: Directory of Vendors, http://pharmacyautomation.com/vendors.html, Jun. 5, 2003—3 pages.

Auto Syringe® AS40A Infusion Pump Technical Manual, 1995, 89 pages, Baxter Healthcare Corporation, Deerfield, IL.

Auto Syringe® AS40A: Model AS40A Infusion Pump Operation Manual, undated, 78 pages, Baxter Healthcare Corporation, Deerfield, IL.

Baxa Corporation, DoseEdge The Leading Edge in Dose Management, Brochure, published copyright date 2010—5 pages.

Baxa Corporation, Product Catalog 2010-2011, published at least by Sep. 15, 2012, https://web.archive.org/web/20120915210739http://www.baxa.com/resources/docs/BaxaCatalog.pdf (52 pages).

Bell Atlantic Healthcare Systems, Inc., court exhibit, StatLan Functions and Features, Specification, release 3.5, dated Nov. 12, 1992, 49 pages.

Ben Schneiderman, "Designing the User Interface: Strategies for Effective Human-Computer Interaction," 2d Ed., 1992, Chapter 5: Direct Manipulation (56 pages), Addison-Wesley Publishing Company.

"Block Medical: Growing with Home Infusion Therapy," taken from Invivo, the Business and Medicine Report, Apr. 1991, pp. 7-9.

Bynum et al., "The Effect of Telepharmacy Counseling on Metered-Dose Inhaler Technique among Adolescents with Asthma in Rural Arkansas", Telemedicine Journal and e-health, vol. 7, No. 3, 2001, Mary AnnLiebert, Inc., pp. 207-218.

Cabral, Jr. et al., "Multmedia Systems for Telemedicine Systems for Telemedicine and Their Communications Requirements," IEEE Communications Magazine Jul. 1996, pp. 20-27.

Cardinal Health Introduces Rxe-source(SM) to Address Pharmacist Labor Shortage and Medication Safety Challenges at Hospitals. PR Newswire, Feb. 25, 2003—5 pages.

Casey, Michelle M. et al., "Pharmacist Staffing and the Use of Technology in Small Rural Hospitals: Implications for Medication Safety" Upper Midwest Rural Health Research Center, Dec. 2005—51 pages.

Charles Safran, M.D. et al., "Computer-Based Support for Clinical Decision Making," Clinical Computin, vol. 7, No. 5 (1990), pp. 319-322.

Clayton M. Curtis, "A Computer-based Patient Record Emerging from the Public Sector: The Decentralized Hospital Computer Program," First Annual Nicholas E. Davies Award Proceedings of the CPR Recognition Symposium, 1995, pp. 75-132, Computer-based Patient Record Institute, Inc., Bethesda, MD.

Clement J. McDonald, M.D. et al., "The Three-Legged Stool: Regenstrief Institute for Health Care," Third Annual Nicholas E. Davies Award Proceedings of the CPR Recognition Symposium, 1997, pp. 131-158, Computer-based Patient Record Institute, Inc., Bethesda, MD.

Clement J. McDonald, M.D. et al., The Regenstrief Medical Record System: 20 Years of Experience in Hospitals, Clinics, and Neighborhood Health Centers,: M.D. Computing, 1992 pp. 206-217, vol. 9, No. 4, Springer-Verlag, New York, NY.

(56) References Cited

OTHER PUBLICATIONS

Clifton, G. Dennis et al., "Provision of pharmacy services to underserved populations via remote dispensing and two-way videoconferencing" Am J Health-Syst Pharm, vol. 60, Dec. 15, 2003 oe pp. 2577-2582.
Dan Murphy, "Nuclear Pharmacy Primer", Radiation Protection Management, vol. 20, No. 5 (2003), pp. 1-10.
Dan Scheraga; "Tech firms answer chain pharmacy's call for productivity," Drug Store News; Dec. 15, 2003; 25, 17; ProQuest Research Library, p. 31-32.
Daniel Andresen et al., "Scalability Issues for High Performance Digital Libraries on the World Wide Web," Proceedings of ADL '96, 1996, pp. 139-148, IEEE.
Daniel J. Nigrin et al., "Glucoweb: A Case Study of Secure, Remote Biomonitoring and Communication," Proceedings of the 2000, 5 pages, American Medical Informatics Association, Bethesda, MD.
Darryl V. Wareham et al., "Combination Medication Cart and Computer Terminal in Decentralized Drug Distribution," American Journal of Hospital Pharmacy, Jun. 1983, pp. 976-978, vol. 40, American Society of Hospital Pharmacists.
Dart, Luann, "Digital Doses" Rural Electric, Jan. 2005—pp. 28-31.
Deborah J. Mayhew, "Principles and Guidelines in Software user Interface Designs," 1992, selected portions of Chapter 9, 17 pages, Prentice-Hall, Inc.
Defendants Initial Invalidity Contentions with Exhibits A and B dated Sep. 8, 2014; Civil Action No. 1:14-cv-00222.
Dennis D. Cote et al., "Robotic system for i.v. antineoplastic drug preparation: Description and preliminary evaluation under simulated conditions," American Journal of Hospital Pharmacy, Nov. 1989, pp. 2286-2293, vol. 46, American Society of Hospital Pharmacists.
Donna Young; "Loan repayments help pharmacists provide care in medically underserved areas," American Journal of Health—System Pharmacy; Nov. 1, 2003, pp. 2186-2188, vol. 60.
Environmental Scan of Pharmacy Technicians; M. MacInnis; Canadian Pharmacists Association; Sep. 2001.
Exhibit 1, Publications Manually Reviewed for the Search to U.S. Pat. No. 8,347,887 titled "System and Method for Remotely Supervising and Verifying Pharmacy Functions" As of Jun. 25, 2014.
Exhibit 1001 U.S. Pat. No. 8,374,887, Alexander issued Feb. 12, 2013.
Exhibit 1002 Patent File History U.S. Pat. No. 8,374,887.
Exhibit 1003, Declaration of Mr. Brian T. Hart from U.S. Pat. No. 8,374,887.
Exhibit 1004, Declaration of Wayne H. Grant from U.S. Pat. No. 8,374,887.
Exhibit 1005, 22 TAC §§291.20, 291.36, and 291.71—291.74 date issued Mar. 5, 2015 from U.S. Pat. No. 8,374,887.
Exhibit 1006 U.S. Pat. No. 6,711,460 Reese issued Mar. 23, 2004 from U.S. Pat. No. 8,374,887.
Exhibit 1009, Peterson et al., The North Dakota Telepharmacy Project: Restoring and Retaining Pharmacy Services in Rural Communities; the journal of Pharmacy Technology, vol. 20, No. 1, Jan./Feb. 2004—pp. 1-39 from U.S. Pat. No. 8,374,887.
Exhibit 1010, Declaration of Benjamin E. Weed from U.S. Pat. No. 8,374,887.
Exhibit 1011, Complaint—*Alexander v. Baxter*, (W.D.Texas 2014) filed Mar. 13, 2014 from U.S. Pat. No. 8,374,887.
Exhibit 1012, Charles F. Seifert et al., "The Training of a Telepharmacist: Addressing the Needs of Rural West Texas," American Journal of Pharmaceutical Education, 2004; 68 (3) Article 60—pp. 1-9 from U.S. Pat. No. 8,374,887.
Exhibit 1013, Assignment Emily H. Alexander to Becton, Dickinson and Company; U.S. Appl. No. 13/747,231; Reel 034110/ Frame 0789 from U.S. Pat. No. 8,374,887.
Exhibit 1014, Exhibit A—Corrected Parties' Claims Construction Terms, Proposed Construction and cites Civil, 1:14cv-00222-LY—pp. 1-7 from U.S. Pat. No. 8,374,887.

Exhibit 1015, Information about Telepharmacy presentation 42503 and Presentation Telepharmacy at Texas Tech; Jon Phillips—1-27 from U.S. Pat. No. 8,374,887.
Exhibit 1017, Declaration of Dr. Roger W. Anderson in Support of Becton, Dickinson & Company's Response to Baxter's Motion for Summary Judgment of Invalidity Based Upon 35 U.S.C. § 101 filed Jan. 15, 2015 from U.S. Pat. No. 8,374,887.
Exhibit 1018, Plaintiff's Claim Construction Brief, 1:14-cv-222-LY filed Oct. 17, 2014 from U.S. Pat. No. 8,374,887.
Exhibit 1019, Plaintiff's Reply Claim Construction Brief, 1:14-cv-222-LY filed Nov. 7, 2014 from U.S. Pat. No. 8,374,887.
Exhibit 1020, The United States Pharmacopeia—the Official Compendia of Standards; 2004 from U.S. Pat. No. 8,374,887.
Exhibit 1021, Curriculum Vitae of Brian T Hart from U.S. Pat. No. 8,374,887.
Exhibit 1022, Curriculum Vitae of Wayne H Grant—Expert oversight-Expert Witness-Litigation Support from U.S. Pat. No. 8,374,887.
Exhibit 1023, Charles D Peterson et al., "The North Dakota Telepharmacy Project: Restoring and Retaining Pharmacy Services in Rural Communities," J Pharm Technol, 2004; vol. 20—pp. 028-039 from U.S. Pat. No. 8,374,887.
Exhibit 1025, Affidavit of Christopher Butler with attached Telemedicine Report Archive dated Mar. 4, 2015—6 pages from U.S. Pat. No. 8,374,887.
Exhibit 1026, Affidavit of Christopher Butler with attached presentation Telepharmacy at Text Tech—Jon Phillips dated Mar. 4, 2015—31 pages from U.S. Pat. No. 8,374,887.
Exhibit 1027, Order on Motion for Summary Judgment filed Aug. 3, 2015 from U.S. Pat. No. 8,374,887.
Exhibit 1028, Final Judgment filed Aug. 3, 2015 from U.S. Pat. No. 8,374,887.
Exhibit 1029 Charles Seifert from U.S. Pat. No. 8,374,887.
Exhibit 1030 Deposition of Charles Seifert Dec. 4, 2015 from U.S. Pat. No. 8,374,887.
Exhibit 1031 Deposition of Diane B. Ginsburg, PhD. Dec. 16, 2015 from U.S. Pat. No. 8,374,887.
Exhibit 1032 Texas Administrative Code, Title 22, Chapter 291, Subchapter A, Section 291.23 as in effect on Feb. 1, 2004 from U.S. Pat. No. 8,374,887.
Felkey, Bill G., "Integrating Technology at the Point of Care", Insight, Jan. 2004—pp. 8-10.
Formula for Patient Safety; ScriptPro; Aug. 17, 2003.
Fred Puckett, "Medication-management component of a point-of-care information system," Am. J. Health-Syst.Pharm., Jun. 15, 1995, pp. 1305-1309, vol. 52, American Society of Health-System Pharmacists, Inc.
"GE ImageQuant TL 7.0 Image Analysis Software" User Manual , May 2007, http://nba.uth.tmc.edu/Assets/pdf/other/typhoon-supporting-files/IQTL-UserManual.pdf, Uppsala, Sweden.
Gerald E. Meyer et al., "Use of bar codes in inpatient drug distribution," Am. J. Hosp. Pharm., May 1991, pp. 953-966, vol. 48, American Society of Hospital Pharmacists, Inc.
Ghent, Natale, "Pharmacists go digital to fight shortage", Pharmacy Practice 20.11 (Nov. 2004): 47—2 pages.
Gilad J. Kuperman, M.D. et al., "Innovations and research review: The impact of the HELP computer system on the LDS Hospital paper medical record," Topics in Health Record Management, 1991, pp. 76-85, vol. 12, Issue 2, Aspen Publishers, Inc.
"Global Med Announces First Safetrace TX™ Sale," Apr. 1, 1999, 2 pages.
Global Med Technologies, Inc. Introduces PeopleMed™.com, inc., A Chronic Disease Management Application Service Provider (ASP) Subsidiary, Jan. 11, 2000, 2 pages, Global med Technologies, Inc., Denver, CO.
Gretchen A. Barry et al., "Bar-code technology for documenting administration of large-volume intravenous solutions," American Journal of Hospital Pharmacy, Feb. 1989, pp. 282-287, vol. 46, American Society of Hospital Pharmacists.
H. Paul Hammann et al., "A World Wide Web Accessible Multi-Species ECG Database," 1997, pp. 7-12, ISA.
Halverson, Daniel R. IsoRx: TelePharmacy Software presentation—23 pages.

(56) References Cited

OTHER PUBLICATIONS

Henry J. Lowe et al., "WebReport: A World Wide Web Based Clinical Multimedia Reporting System," 1996, pp. 314-318, AMIA, Inc.

"Hospitals battle errors with bar codes," Mar. 24, 2004, 3 pages, MSNBC.

Howard L. Bleich et al., "Clinical Computing in a Teaching Hospital," Use and Impact of Computers in Clinical Medicine, 1987, pp. 205-223 and selected p. Springer—Verlag, New York, NY.

http://isorx.com/ Jan. 29, 2004.

http://www.scriptpro.com/products//sp-200/main.htm, Feb. 13, 2004, Product listing for SP 200® Robotic Prescription Dispensing System.

http://www.scriptpro.com/products/space/space200.htm, Feb. 10, 2004, Product listing for SP Automation Center 200TM (Space 200TM) Prescription Dispensing Automation Center.

Hughes, Shirley, "Bedside Terminals: Clinicom," Clinical Computing, Jan./Feb. 1988, pp. 22-28, vol. 5, No. 1.

IPR Decision Paper No. 8 Entered Aug. 13, 2015 from U.S. Pat. No. 8,374,887.

IPR Final Written Decision Paper No. 29 Entered Jul. 11, 2016 from U.S. Pat. No. 8,374,887.

James Kazmer et al., "The Creation of Virtual Electronic Medical Record," 1996, 17 pages.

Jennifer Langham; "Taking Automation to New Levels," Insight, the QS/1 Magazine, Oct. 2002; pp. 2-5.

John Frady; "What's New in RxCare Plus 17.2," Insight, the QS/1 Magazine, Apr. 2002; pp. 2-3, 14.

Jones, et al., "Use of a remote computerized system for study documentation in clinical trials" Drug Information Journal, Oct.-Dec. 1998, vol. 32, No. 4 oe pp. 1153-1163.

Karen E. Bradshaw et al., "Physician decision-making—Evaluation of data used in a computerized ICU," International Journal of Clinical Monitoring and Computing, 1984, pp. 81-91, vol. 1, Martinus Nijhoff Publishers, Netherlands.

Kastango, Eric S. and Bradshaw, Brian D., "USP chapter 797: Establishing a practice standard for compounding sterile preparations in pharmacy" Am J Health-Syst Pharm., Sep. 15, 2004, vol. 61—pp. 1928-1938.

Kenneth N. Barker et al., "Effect of an automated bedside dispensing machine on medication errors," American Journal of Hospital Pharmacy, Jul. 1984, pp. 1352-1358, vol. 41, No. 7, American Society of Hospital Pharmacists.

Keeys, Christopher A. et al., "Providing nighttime pharmaceutical services through telepharmacy" Am J Health-Syst Pharm, Apr. 15, 2002, vol. 59—pp. 716-721.

Khan, Shamima et al., "Is There a Successful Business Case for Telepharmacy?" Telemedicine and e-Health, vol. 14, No. 3, Apr. 2008, pp. 235-245.

Kimber, Michael B. et al., "Telepharmacy-Enabling Technology to Provide Quality Pharmacy Services in Rural and Remote Communities" Journal of Pharmacy Practice and Research, vol. 36, No. 2, 2006—128-133.

Kodak DirectView PACS—Rural Hospital Joins the Big Leagues PACS/Enterprise Information management (EIM) Solution—www.kodak.com/go/medical—4 pages.

Kosub, David, "Device allows pharmacy care in remote areas" Pharmacy Practice, vol. 20, No. 10, Oct. 2004—pp. 12-13.

Koutnik, Eileen, Assistnat Editor, Pharmacy Times, "The Pharmacy of Tomorrow" Pharmacy Times, Aug. 1, 2003—3 pages.

Larry B. Grandia, B.S.E et al., "Building a computer-based Patient Record System in an Evolving Integrated Health System," First Annual Nicholas E. Davies Award Proceedings of the CPR Recognition Symposium, 1995, pp. 19-55, Computer-based Patient Record Institute, Inc., Bethesda, MD.

Lefkowitz, Sheldon et al., "A Trial of the Use of Bar Code Technology to Restructure a Drug Distribution and Administration System," 1991, pp. 239-242, Hospital Pharmacy, vol. 26.

LP, "ATM-STyle Drug Dispensers Taking Hold in Areas With Limited Pharmacist Services" Pharmacy Practice News, Jan. 2004, vol. 31, No. 1—4 pages.

"The Longitudinal Clinical Record: A View of the Patient," taken from Proceedings of the 1994 Annual HIMSS Conference, Feb. 14, 1994, pp. 239-250, Healthcare Information and Management Systems Society, Chicago, Illinois, USA.

Lustig, Ahuva, "Medication error prevention by pharmacists—An Israeli solution" Pharmacy World & Science, 2000, vol. 22, No. 1—pp. 21-25.

Medicaid Memo—Department of Medical Assistance Services (Converting NDCs from 10-digits to 11-digits) May 31, 2007.

Medcin® Technical Overview, undated, 111 pages, Medicomp Systems.

Michael H. Mackin, "Impact of Technology on Environmental Therapeutic Device Design," Medical Instrumentation, Feb. 1987, pp. 33-35, vol. 21, No. 1, Association for the Advancement of Medical Instrumentation.

Michelle M. Casey, M.S., Jill Klingner, R.N., M.S., and Ira Moscovice, Ph. D.; "Access to Rural Pharmacy Services in Minnesota, North Dakota, and South Dakota," Working Paper Series, Jul. 2001, #36.

Monane et al., "Improving Prescribing Patterson for the Elderly Through an Online Drug Utilization Review Intervention", JAMA, Oct. 14, 1998, vol. 280, No. 14—pp. 1249-1252.

Morris, Aisha M., Schneider, Philip J., Pedersen, Craig A. and Mirtallo, Jay M. "National survey of quality assurance activities for pharmacy-compounded sterile preparations" Am J Health-Syst Pharm, Dec. 15, 2003, vol. 60—pp. 2567-2576.

Murray, Michael D. et al. "Effects of Computer-based Prescribing on Pharmacist Work Patterns" Journal of the American Medical Informatics Association, Nov./Dec. 1998, vol. 5, No. 6—pp. 546-553.

Napoli, M et al., "Picture archiving and communication in radiology", Rays. Jan.-Mar. 2003—PubMed—NCBI http://www.ncbi.nlm.m=nih.gov/pubmed/14509181—Abstract.

Nissen et al., Can telepharmacy provide pharmacy services in the bush, School of Pharmacy, University of Queensland, Brisbane, Australia, Journal of Telemedicine and Telecare 2003, vol. 9 (Suppl. 2): S2:39-41.

North Dakota Century Code Statute Law—State Board of Pharmacy—219 pages.

Parks, Liz, "Annual report of retail pharmacy: Using central-fill to maximize dispensing" Drug Store News, Aug. 20, 2001 vol. 24, No. 11—pp. 51, 75.

Parsons, et al., "Digital Media-Can I Change a Graphic's File Size?", New Perspectives on Computer Concepts-Course Technology, 2011, Cengage Learning, Boston, MA.

Paul H. Perlstein et al., "Computer-Assisted Newborn Intensive Care," Pediatrics, Apr. 1976, pp. 494-501, vol. 57, No. 4, American Academy of Pediatrics, Inc., Evanston, Illinois.

Paul H. Perlstein et al., "Future Directions for Device Design and Infant Management," Medical Instrumentation, Feb. 1987, pp. 36-41, vol. 21, No. 1, Association for the Advancement of Medical Instrumentation.

PCA II Multi-Mode Cartridge Operator's Manual, Sep. 1995, approx. 40 pages, Baxter Healthcare Corporation, Deerfield, IL.

Pesce, James, "Bedside Terminals: Medtake," Clinical Computing, Jan. /Feb. 1988, pp. 16-21, vol. 5, No. 1.

Peter Lord et al., MiniMed Technologies Programmable Implantable Infusion System, Annals New York Academy of Science, pp. 66-71, describing clinical trials from Nov. 1986.

Peterson et al., The North Dakota Telepharmacy Project Restoring and Retaining Pharmacy Services in Rural Communities—Presentation North Dakota State University, Fargo, North Dakota.

Petition for Inter Partes Review *Baxter International Inc.* v. *Becton, Dickinson and Company* for U.S. Pat. No. 8,374,887, pp. 1-69.

Pharmacy Automation Online Vendors Page; Internet Archive Wayback Machine; http://pharmacyautomation.com/vendors.html—3 pages.

Pharmacy Data Management (PDM) Technical Manual/Security Guide Version 1.0, Sep. 1997—55 pages.

Pharmacy education and practice out of sync? (Roundtable) Chain Drug Review, vol. 25, No. 6, Mar. 17, 2003, RX2 (6).

(56) References Cited

OTHER PUBLICATIONS

Prem S. Chopra, Virgil A. Thomason, and Dell M. Stinett; "Voice-Activated Networked Workstation for a Physically Disabled Physician," 10-7803-2050-6/94 1994 IEEE, pp. 478-479.
Product literature, Baxter Healthcare Corporation, "Flo-Gard® 6201 Volumetric Infusion Pump," 1992, 2 pages.
Product literature, Baxter Healthcare Corporation, "MultiPlex™ Series 100 Fluid Management System," 1988, 2 pages.
Product literature, Baxter Healthcare Corporation, "MultiPlex™ Series 100 Fluid Management System," undated, 2 pages.
Remote Dispensing Regulations, NABPLAW Sep. 2003.
Woodall, Sandra C., Remote Order Entry and Video Verification; Reducing After-Hours Medication Errors in a Rural Hospital; S. Woodall; Joint Commission on Accreditation of Healthcare Organizations; vol. 30; No. 8; Aug. 2004.
Rich Muller; "NRx QS/1's Premium Pharmacy Software," Insight, the QS/1 Magazine, Jul. 2003; pp. 2-3, 12-15.
Rouse, et al., Academy of Managed Care Pharmacy et al., "White paper on pharmacy technicians 2002: Needed changes can no longer wait" Am J Health-Syst Pharm, Jan. 1, 2003, vol. 60—pp. 37-51.
Rule Section 291.36—Class A Pharmacies Compounding Sterile Pharmaceuticals—1 page.
Schrenker, Richard and Cooper, Todd, "Building the Foundation for Medical Device Plug-and-Play Interoperability".
Standard Specification for Transferring Clinical Laboratory Data Messages Between Independent computer Systems, Annual Book of ASTM Standards, Mar. 25, 1988, pp. 1-16, E 1238-88, Global Engineering Documents, Philadelphia, PA.
Standard Specification for Transferring Clinical Observations Between Independent Computer Systems, Annual Book of ASTM Standards, Jun. Mar. 1994, pp. 132-210, E 1238-94, Philadelphia, PA.
Standard Specification for Transferring Clinical Observations Between Independent Computer Systems, Aug. 10, 1997, 79 pages, ASTM E 1238-97, West Conshohocken, PA, United States.
Standard Specification for Transferring Information Between Clinical Instruments and Computer Systems, Annual Book of ASTM Standards, Jun. 1991, 15 pages, E 1394-91, Philadelphia, PA.
Suzanne Carter, RN, Ed.D et al., "The Computer-based Patient Record: The Jacobi Medical Center Experience," Second Annual Nicholas E. Davies Award Proceedings of the CPR Recognition Symposium, 1996, pp. 71-95, Computer-based Patient Record Institute, Inc., Bethesda, MD.
T. Allan Pryor et al., "help—A Total Hospital Information System," Proceedings of the Fourth Annual Symposium on Computer Applications in Medical Care, Nov. 2-5, 1980, pp. 3-7, vol. 1, Institute for Electrical and Electronics Engineers, New York, NY.
T.E. Bozeman et al., "The Development and Implementation of a Computer-Based Patient Record in a Rural Integrated Health System," Third Annual Nicholas E. David Award Proceedings of the CPR Recognition Symposium, 1997, pp. 101-130, Computer-based Patient Record Institute, Inc., Bethesda, MD.
"Telepharmacy project expands students' practice experience" Telemedicine Report, vol. 6, No. 1, Jan. 2004 oe 4 pages.
The World's First Fully Integrated Workflow Manager for I.V. Rooms, IntelliFlowRx Brochure, For Health Technologies Inc,. United States, May 2008.
Title 22. Examining Boards, 22 TAC Section 1.161; texinfo.library.unt.edu/Texasregister/html/2001/sep-14/PROPOSED/22.EXAMING BOARDS.html—Sep. 20, 2014, pp. 1-70.
Ukens, Carol, "Pharmacist shortage boosts telepharmacy" Drug Topoics, Jun. 3, 2002; 146, 11—p. 53.
Valeriy Nenov et al., "Remote Analysis of Physiological Data from Neurosurgical ICU Patients," Journal of the American Medical Informatics Association, Sep./Oct. 1996, pp. 318-327, vol. 3, No. 5.
Victor J. Perini et al., "Comparison of automated medication-management systems,: Am. J. Hosp. Pharm., Aug. 1, 1994, pp. 1883-1891, vol. 51, American Society of Hospital Pharmacists, Inc."

Vincenzo Della Mae et al., "HTML generation and semantic markup for telepathology," Computer Networks and ISDN Systems, 1996, pp. 1085-1094, vol. 28, Elsevier Science B.V.
Website information for Cartharsis Medical Technology Products, Dec. 9, 2001, 15 pages.
Website information for MedPoint™, Mar. 13, 2003, 20 pages, Bridge Medical, Solana Beach, CA.
William R. Dito et al., "Bar codes and the clinical laboratory: adaptation perspectives," Clinical Laboratory Management Review, Jan./Feb. 1992, pp. 72-85, Clinical Laboratory Management Association, Inc.
Wills, Robert D., "Drug Images and Drug Imprints" Insight, Apr. 2001—p. 7.
Yvonne Mari Abdoo, "Designing a Patient Care Medication and Recording System that Uses Bar Code Technology," Computers in Nursing, May/Jun. 1992, pp. 116-120, vol. 10, No. 3.
Jon Phillips, Telepharmacy at Texas Tech, PowerPoint, Jan. 26, 1997, https://web.archive.org/web/20040509162423/http:/www.ttuhsc.edu/telemedicine/Powerpoint/Telepharmacy%20presentation %2042503.ppt.
A.H. McMorris et al. "Are Process Control Rooms Obsolete?", Control Engineering, pp. 42-47, Jul. 1971.
Standard Specification for Transferring Clinical Observations between Independent Computer Systems, Annual Book of ASTM Standards, Nov. 14, 1991, pp. 1-64, ASTM E 1238-91, Philadelphia, PA.
Standard Specification for Transferring Information Between Clinical Instruments and Computer Systems, Dec. 10, 1997; 15 pages, ASTM E 1394-97, West Conshohocken, PA, United States.
Web site information, Information Data Management, Inc.'s PCMS: Plasma Center Management System, Dec. 14, 2001, 11 pages.
Web site Information, Wyndgate Technologies' SafeTrace Tx™, undated, 15 pages.
Specification for Low-Level Protocol to Transfer Messages Between Clinical Laboratory Instruments and Computer Systems, Mar. 11, 1991; 7 pages, ASTM E 1381-91, Philadelphia, PA, United States.
Atherton, H.D., Dollberg, S., Donnelly, M.M., Perlstein, P. H. Roath, S.B., "Computerized Temperature Control of the Low-Birth-Weight Infant: A 20-Year Retrospective and Future Prospects," Biomedical Instrumentation and Technology, Jul./Aug. 1994, pp. 302-309, vol. 28 No. 4.
Friesdorf, W., Grob-Alltag, F., Konichezky, S., Schwilk, B., Fattroth, A., Fett, P., "Lessons learned while building an integrated ICU workstation," International Journal of Clinical Monitoring and Computing, 1994, pp. 89-97, vol. 11.
Gammon, K., Robinson, K., "Bedside Data System Aids Pharmacy," Computers in Healthcare, Dec. 1988, pp. 35-37, vol. 9 No. 12.
Graseby 3100 Syringe Pump, Graseby Medical Ltd., A Cambridge Electronic Industries Company, England, 2 pages.
Kampmann, J., Lau, G., Kropp, St., Schwarzer, E., Hernandez Sande, C., "Connection of electronic medical devices in ICU according to the standard 'MIB'," International Journal of Clinical Monitoring and Computing, 1991, pp. 163-166, vol. 8.
Angaran, "Telemedicine and telepharmacy: Current status and future implications", Am J Health-Syst Pharm, vol. 56, Jul. 15, 1999 (32 pages).
Carson, Ewart et al., "A Systems Methodology for the Development and Evaluation of a Telematic Home Haemodialysis Service," Proceedings—19th International Conference—IEEE/EMBS Oct. 30-Nov. 2, 1997, Chicago, Illinois, pp. 907-910.
Japanese Office Action for related Japanese Application No. 2017-522051; action dated Oct. 1, 2019; (4 pages).
Singapore Written Opinion for related Singapore Application No. 11201703338P; action dated Jun. 24, 2019; (7 pages).
Extended European Search Report from corresponding European Patent Application No. 20193098.9, mailed Dec. 8, 2020.
Australian Examination Report for related Australian Application No. 2015335629; report dated Jun. 5, 2020; (5 pages).
New Zealand Examination Report for related New Zealand Application No. 731172; action dated Aug. 2, 2021; (5 pages).
Canadian Office Action for related Canadian Application No. 2,965,533; action dated Sep. 13, 2021; (5 pages).

(56) References Cited

OTHER PUBLICATIONS

Office Action for related Japanese Application No. 2021-123427; action dated Sep. 13, 2022; (3 pages).

Office Action for related Canadian Application No. 2,965,533; action dated Jan. 28, 2023; (5 pages).

*Becton, Dickinson and Company, Appellant* v. *Baxter Corporation Englewood*, Appelle, Case No. 2020-1937 Appeal from the United States Patent and Trademark Office, Patent Trial and Appeal Board in No. IPR2019-00119—Decided: May 28, 2021—Document 30 filed May 28, 2021—21 pages.

*Becton, Dickinson and Company*, Petitioner, v. *Baxter Corporation Englewood*, Patent Owner, IPR2019-00212, U.S. Pat. No. 9,474,693 B2 Judgment Final Written Decision Determining All Challenged Claims Unpatentable 35 U.S.C. Section 318(a)—Denying Patent Owner's Revised Motion to Amend to Substitute Claims 20-38 35 U.S.C. Section 318(a)—Denying Petitioner's Motion to Exclude Evidence 37 C.F.R. Section 42.64—Paper No. 63 dated Apr. 29, 2020—102 pages.

*Becton, Dickinson and Company, Petitioner*, v. *Baxter Corporation Englewood*, Patent Owner, IPR2019-00119, U.S. Pat. No. 8,554,579 B2 Judgment Final Written Decision Determining No Challenged Claims Unpatentable 35 U.S.C. Section 318(a)—Denying Petitioner's Motion to Exclude Evidence 37 C.F.R. Section 42.64, Paper 51 entered Apr. 29, 2020—63 pages.

*Baxter Corporation Englewood*, Appellant v. *Becton, Dickinson and Company*, Appellee, Case Nos. 2020-1806, 2020, 1808, Judgment Document 40 filed/entered Mar. 8, 2021 IPR2019-00120, IPR2019-00212 *Baxter Corporation Englewood*, Appellant v. *Becton, Dickinson and Company*, Appellee, Case Nod. 2020-1806, 2020, 1808, Mandate entered Mar. 8, 2021 Document 43, filed May 17, 2021 IPR2019-00120, IPR2019-00212.

*Becton, Dickinson and Company*, Petitioner, v. *Baxter Corporation Englewood*, Patent Owner, IPR2019-00120 U.S. Pat. No. 9,662,273 B2 Judgement Final Written Decision Determining Challenged Claims Unpatentable 35 U.S.C. Section 318 (a)—Denying Patent Owner's Revised Motion to Amend to Substitute Claims 22-42 35 U.S.C. Section 318(a) Denying Petitioner's Motion to Exclude Evidence 37 C.F.R. Section 42.64—Paper 63 dated Apr. 29, 2020, 90 pages.

*Baxter Corporation Englewood*, Appellant v. *Becton, Dickinson and Company*, Appellee, Case Nos. 2020-1806, 2020-1808 IPR2019-00120-IPR2019-0012, On Petition for Rehearing En Banc, Order—Document 42, filed May 10, 2021—2 pages.

*Baxter Corporation Englewood*, Appellant, v. *Becton, Dickinson and Company*, Appellee, Case Nos. 20-1806, 20-1808 Inter Partes Review Nos. IPR2019-00120, IPR2019-00121—Petition for Rehearing En Banc By Appellant Baxter Corporation Englewood—Document 41, filed Apr. 7, 2021—18 pages.

Inter Partes Review Certificate, Ranalletta et al. U.S. Pat. No. 9,662,273 K1 Certificate issued Dec. 30, 2021—2 pages.

Inter Partes Review Certificate, Tribble et al. U.S. Pat. No. 8,554,579 K1 Certificate issued May 12, 2022—2 pages.

\* cited by examiner

AUTOMATED EXCHANGE OF HEALTHCARE INFORMATION FOR FULFILLMENT OF MEDICATION DOSES

CROSS-REFERENCE TO RELATED APPLICATION

This application claims priority from U.S. Provisional Application No. 62/068,301 filed on Oct. 24, 2014, entitled "AUTOMATED EXCHANGE OF HEALTHCARE INFORMATION FOR FULFILLMENT OF MEDICATION DOSES," the contents of which are incorporated by reference herein as if set forth in full.

BACKGROUND

Despite advances in electronic healthcare information systems, processes related to the exchange of information may still rely upon manual intervention by a human user. While independent systems may be operative to maintain an electronic medical record (EMR), the exchange of information between independent systems may be complicated by a lack of a standardized data format or data exchange protocol. Furthermore, to the extent data may be exchanged between independent systems, use of unique semantics at each independent system may result in complications when exchanging data therebetween.

For example, in the context of dose order processing, a physician or the like may rely upon a hardcopy order form to request a medication order to be administered to a patient. In turn, the hardcopy of the order form may provided to a pharmacy by way of, for example, physical transport, facsimile, relay by telephone, relay by email, etc. In turn, upon receipt of the information related to the dose order at the pharmacy, a technician may be required to manually input the information (e.g., by transcribing information from the hardcopy or an electronic copy thereof) regarding the requested dose order. As such, a new instance of an EMR related to the dose order requested based on the transcribed dose order may be generated in the pharmacy. In turn, the dose order may be fulfilled by the pharmacy (e.g., including calculation, review, compounding, and delivery of the dose order).

As such, at one or more instances during the dose ordering process, information related to the requested dose order may be required to be manually processed by a human user. For example, a human user may be required to relay information from a physical hardcopy order form to a pharmacy system. Furthermore, a human user may be required to retrieve information from a first system and transcribe information into a second system. For example, a human user may be required to input received order information into a pharmacy information system (PIS). In this regard, despite advances in EMR systems for dose order generation and pharmacy fulfillment, the exchange of healthcare information may still be subject to human user handling.

In turn, the potential for delays and errors may be compounded because of the requirement for human intervention. For example, it is been found that 60% of clinicians working with parenteral nutrition orders report one to five ordering errors per month. Significantly, near fatal complication or death may result in 4.8% of parenteral nutrition order errors in one two year span that was reviewed. Further still, transcription may provide delay in order fulfillment as it has been found that up to 10% of parenteral nutrition orders require clarification. The most common causes of the need for clarification include illegible writing, missing essential ingredients, or unstable macronutrient content. In this regard, human errors may come in the form of transcription errors, EMR order entry errors, errors resulting in information asymmetry, errors resulting in order form legibility, errors related to reentry of orders in the pharmacy system, or other points within a data flow that require human intervention. Accordingly, improvements in exchange of healthcare information between independent healthcare systems may reduce the reliance upon human intervention, thereby reducing error rates in improving patient outcomes.

SUMMARY

In view the foregoing, the present disclosure is generally related to improved exchange of healthcare information. Specifically, the present disclosure presents systems and methods that may at least in part help reduce reliance upon manual human interaction in the exchange of healthcare information between independent healthcare systems. In turn, the reliance upon human interaction to facilitate information exchange may be reduced, and the speed and accuracy at which healthcare information may be exchange between independent healthcare systems may be improved. In turn, an at least partially automated approach to healthcare information exchange may be facilitated.

Accordingly, use of an automated health information exchange as described herein may improve patient outcomes by assisting in reduction of errors associated with human interaction in the exchange of healthcare information. Furthermore, the speed at which information may be exchanged may be increased for more efficient pharmacy operation. For instance, one context in which automated healthcare information exchange may be utilized is in the context of dose order fulfillment. Specifically, automation of the exchange of healthcare information from dose order entry to dose order fulfillment may be facilitated to assist in reduction of (and potentially elimination of) the need for human intervention in connection with the exchange of healthcare information between an EMR system that facilitates dose order entry, pharmacy information systems (PIS) for management of pharmacy operations, and dose fulfillment clients for use in fulfillment of medication doses that are to be administered to a patient. As discussed herein, dose orders may relate to requested medication doses in any number of contexts including, for example, IV doses, parenteral nutrition (PN) doses, total parenteral nutrition (TPN) doses, or the like.

Specifically, the disclosure presented herein may facilitate receipt and processing of a healthcare information data stream by a platform interface module. The platform interface module may perform identification and parsing of the healthcare information data stream to identify individual dose orders from the healthcare information data stream. In this regard, the healthcare information data stream may include a multitude of data including, for example, a plurality of dose orders or other data related to EMR data or hospital information system (HIS) data. Upon identification of a dose order from the healthcare information data stream, the platform interface module may be operative to parse the dose order such that dose order data fields may be identified and populated with dose order metadata related to the dose order. The dose order data fields may correspond to dose order characteristics such as an ingredient list, product requirements, administration characteristics, patient information, or other appropriate data types related to the dose order. In turn, corresponding dose order metadata for each respective dose order may be parsed by the platform interface module. A staging table may be generated and stored at the platform interface module in relation to a dose order. The staging table may include a standardized intermediate format for storage of dose order metadata in corresponding relation to dose order data fields for a given dose order.

In this regard, it may be appreciated that different various EMR systems (e.g., one or more HISs, one or more physician order entry (POE) systems, or the like) may be used to generate and/or transmit dose orders to a pharmacy. In turn, receipt and processing of the health information data stream to generate staging tables may facilitate generation of a standardized intermediate format for the dose order. The standardized intermediate format may be beneficial as the dose order may be routed to one of a plurality of different dose order fulfillment clients for use in fulfillment of the medication dose associated with the dose order. In turn, rather than having to facilitate specific respective correlations between different EMR system formats and specific dose fulfillment client input formats, the standardized intermediate form (e.g., the staging table) may be utilized such that a plurality of different EMR system formats may be standardized into the standardized intermediate form and the standardized intermediate form may be in turn transformed into one of the plurality of different input formats associated with different respective ones of dose fulfillment clients. In this regard, upon addition of different EMR systems, the data from the EMR system may be standardized into the standardized intermediate format such that the system may process dose orders received from the new EMR system without having to generate application functionality specific to each dose fulfillment client for the new EMR system. Furthermore, as new dose fulfillment clients are added the system, transformation of the data in the standardized intermediate format may be accomplished without having to generate application functionality for the new dose fulfillment client specific to each EMR system. Accordingly, a robust and modular data exchange system may be realized that allows for any one of a plurality of EMR systems to be utilized in conjunction with any one of a plurality of dose fulfillment clients.

In at least some embodiments, the dose order records maintained in a staging table may have some dose order management functionality applied thereto. For example, functions in connection with viewing, modifying, prioritizing, or otherwise organizing the dose orders may be applied to the dose order information stored in the staging tables. In turn, improved pharmacy management may be provided in that personnel associated with the operation of the pharmacy may be able to perform pharmacy management functions collectively on the dose orders stored in the staging tables. For instance, such pharmacy management may be performed on the dose orders prior to provision of the dose orders to a plurality of dose fulfillment clients. Further still, dose order management may be performed locally relative to one or more dose fulfillment clients. In turn, pharmacy resources may be efficiently managed in connection with dose orders having different priorities, urgencies, or the like.

Dose order information from the staging table may be retrieved by and/or provided to a dose fulfillment client for use in preparation of a dose associated with the dose order. In this regard, the dose order information in the staging table may be transformed from the standardized intermediate form of the staging table into an input format associated with a dose fulfillment client. For instance, a unique input format for a given dose fulfillment client may be provided. As such, identification of a specific dose fulfillment client for use in preparation of the dose order may allow for the corresponding unique input format associated with the identified dose fulfillment client to be used to transform the data from the staging table into the unique input format for a given client.

In connection with the transformation of information from the staging table into the dose from a client specific format, a mapping and/or translation processes may occur. For example, the transformation of the dose order information from the standardized intermediate format to the unique input format for a given dose fulfillment client may include mapping dose order data fields from the staging table to corresponding respective dose fulfillment client input fields. In addition to the specific mapping, translations of the data may be performed. For example, the unique input format for a dose fulfillment client may specify a form in which the data is expected. As such, data may be translated from the form in which it is provided in the staging table such that the data complies with the form of the unique input format.

Additionally, dose order metadata related to the corresponding respective dose fulfillment client input fields may be validated to determine whether a valid input is provided for the dose order from the staging table. In the event the data may not be validated (e.g., due to a parsing error, a mapping error, a translation error, or some other error), exception processing may occur. That is, exception processing may allow for a user to resolve any errors identified during validation, mapping, or translation. The resolution of the errors by a user may be used to modify processing rules (e.g., validation rules, mapping rules, or translation rules) or the like for subsequent dose orders. The receipt of an input corresponding to a resolution of an error by a user may be incorporated into the transformation and/or validation of subsequent orders. Thus, in connection with the transformation process, exceptions related to the mapping, translation, and/or validation of dose order metadata from the staging table may be processed as will be discussed herein. Furthermore, logistical processing may be performed such that changes, cancellations, or other modifications to a dose order received during the processing of the dose order may be facilitated. The exemption and/or logistical processing may be performed at the same location or different locations. Furthermore, the exemption and/or logistical processing may occur at the platform interface module, transformation module, and/or dose fulfillment client.

In addition, logging may occur throughout the exchange of healthcare data between independent systems described herein. In turn, auditing, troubleshooting, or the like may be facilitated for any or all of the steps of the exchange between systems described herein. The log information generated during the healthcare information exchange may be maintained at each independent system or aggregated into a single repository related to a portion of or the entire path of the data exchange. In turn, improve record-keeping for the purposes of auditing or the like may provided in connection with the exchange of healthcare information between systems described herein.

As contemplated herein, a plurality of dose fulfillment clients may be employed in connection with the healthcare information exchange facilitated by the disclosure presented herein. For instance, dose fulfillment clients may include a pharmacy workflow management application for use in manual preparation of dose orders, automated syringe filling platforms, TPN management modules, automated compounders (e.g., for use in fulfilling PN and TPN orders), automated dose dispensing cabinets, or other dose fulfillment clients that may be utilized to realize a physical dose associated with the dose order. Accordingly, at least some of the dose fulfillment clients may comprise automated dose preparation systems for fulfillment of dose orders without the need for human intervention. In turn, in at least some embodiments facilitated herein, the processing performed on the dose order may be completely automated such that there is no human intervention between the entry of the dose order by a physician or the like and the fulfillment of the dose order by an automated dose fulfillment client.

A first aspect of the disclosure presented herein includes a method for automated transformation of healthcare information by a transformation module between a first form from an electronic medical record (EMR) system and a second form associated with a dose fulfillment client for preparation of a dose in accord with a dose order of the health information data. The method includes retrieving dose order metadata, at a transformation module, for a dose order from a staging table corresponding to the dose order. The staging table is populated with dose order metadata received from a healthcare information data stream in a first form from the EMR system. Additionally, the staging table includes a plurality of dose order data fields populated with corresponding respective portions of the dose order metadata. The method further includes transforming the dose order metadata into a predefined second form corresponding with a dose fulfillment client and providing the dose order metadata in the second form to the dose fulfillment client for fulfillment of a dose associated with the dose order based on the dose order metadata.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, the method may further include receiving the healthcare information data stream at a platform interface module from the EMR system. The healthcare information data stream may include information related to the dose order (e.g., among other information related to different dose orders and/or unrelated data). The method may also include identifying the dose order from the healthcare information data stream and parsing the dose order metadata for the dose order from the healthcare information data stream. The dose order metadata may include one or more dose characteristics associated with the dose order. The method may further include populating the staging table, stored in a staging table database at the platform interface module, with the dose order metadata for the dose order.

The staging table may store the dose order metadata a standardized intermediate format. For example, the method may further include receiving a first dose order in a first EMR form and receiving a second dose order in a second EMR form. The first dose order and the second dose order may correspond to a dose order with identical constituent ingredients. The form of the constituent ingredients in the first EMR form may differ from the second EMR form (e.g., because of different EMR sources or different EMR formats utilized). The form of the constituent ingredients for the first dose order may, in turn, be identical to the form of the constituent ingredients for the second dose order in the respective staging tables corresponding to the first dose order and the second dose order. Furthermore, other dose data may be standardized such as, for example, patient data, dose administration data, or the like.

The method may also include identifying, at least in part based on the dose order metadata, the dose fulfillment client from a plurality of dose fulfillment clients for fulfillment of the dose order. As such, the plurality of dose fulfillment clients each have respective predefined second forms. In turn, the transforming may at least in part be based on the respective predefined second form of the identified dose fulfillment client. The staging table may be independent of any of the plurality of dose fulfillment clients.

The transforming may include mapping the plurality of dose order data fields of the staging table to corresponding respective ones of a plurality of dose fulfillment client input fields. In an application, the dose fulfillment client input fields may be defined by a unique input format associated with the dose fulfillment client. The transforming may additionally include validating the dose order metadata of the plurality of dose order data fields with respect to the unique input format for corresponding ones of the dose fulfillment client input fields. The validating may include correlating the dose order metadata of the plurality of dose order data fields to formulary records of the dose fulfillment client with respect to the corresponding respective ones of the dose fulfillment client input fields.

In an embodiment, the method may include exception processing (e.g., in response to the validating, mapping, or translating of dose order data). In this regard, the method may include generating an exception in response to an error associated with at least one of the mapping or validating. Additionally, the exception may include prompting a human user to resolve the error. As such, the method may include receiving, from the human user, an input associated with the resolution of the error. In turn, the input may include at least one of a correct mapping between a dose order data field of the staging table and a corresponding respective one of a dose fulfillment client input fields or a correct correlation between a portion of dose order metadata and a formulary record of the dose fulfillment client. As such, the exception processing may further include updating at least one of a mapping logic or a correlation logic for use in the mapping and correlating, respectively, based on the input received from the human user.

In an embodiment, the method may include updating the staging table to indicate the dose order metadata for the dose order has been retrieved by the dose fulfillment client. As such, the processing status of a dose may be maintained at the staging table to provide an indication of dose orders that have been processed and those that have not been processed. The method may also include managing the dose order (e.g., by organizing, prioritizing, etc.) prior to providing the dose order metadata in the second form to the dose fulfillment client. For instance, the managing may include providing a user interface to allow a user to perform a management function relative to the dose order. Specifically, the managing may include at least one of modification of dose order metadata, cancellation of the dose order, organization of the dose order relative to other dose orders, or prioritization of the dose order relative to other dose orders.

Additionally, the method may include performing logistical processing on the dose order. The logistical processing may include performing an action relative to the dose order in response to receipt of an EMR system message subsequent to the receipt of the dose order. The EMR system message may include at least one of a dose order change message or a dose order discontinuation message. As such, the logistical processing may include determining if the dose order metadata has been provided to the dose fulfillment client, and wherein the logistical processing is at least in part based on whether the determining. The logistical processing may include performing an action relative to the dose order record corresponding to the EMR system message for a dose order record that has not yet been provided to the dose fulfillment client. For instance, the logistical processing may include providing data to the dose fulfillment client related to the EMR system message for a dose order record that has been provided to the dose fulfillment client. The data provided to the dose fulfillment client related to the EMR system message may also be transformed into a form corresponding to the dose fulfillment client.

In an embodiment, the dose fulfillment client may include at least one of a pharmacy workflow management application for manual preparation of the dose order, an automated dose preparation device, an automated total parenteral nutrition (TPN) compounder, or a dose dispensing cabinet. Additionally, the EMR system may include a hospital information system (HIS). As such, the method may include exchange of a message from independent healthcare systems comprising the EMR system and the dose fulfillment client. The data exchanged between the EMR system and the dose fulfillment client may be otherwise incompatible without the use of the healthcare information exchange system. For instance, the healthcare information data stream may be a Health Level 7 (HL7) format.

The method may also include logging activity taken with respect to the dose order to generate a log regarding activities relative to the dose order. The logging may include aggregating a plurality of logs generated relative to different respective actions taken with respect to the dose order.

A second aspect includes a method for automated exchange of healthcare information between an electronic medical record (EMR) system and a dose fulfillment client for fulfillment of a dose order. The method includes receiving a healthcare information data stream at a platform interface module. The healthcare information data stream includes information related to a dose order. The method also includes identifying the dose order from the healthcare information data stream and parsing dose order metadata for the dose order from the healthcare information data stream. The dose order metadata includes one or more dose characteristics associated with the dose order. The method further includes populating a staging table with the dose order metadata for the dose order. The staging table includes a plurality of dose order data fields populated with corresponding respective portions of the dose order metadata. The method further includes transforming the dose order metadata into a predefined format corresponding to a particular dose fulfillment client to generate transformed dose order metadata. Also, the method includes providing the particular dose fulfillment client access to the transformed dose order metadata, wherein the dose fulfillment client is operable to retrieve the transformed dose order metadata from the staging table to fulfill the dose order based on the transformed dose order metadata.

A number of feature refinements and additional features are applicable to the second aspect. These feature refinements and additional features may be used individually or in any combination. As such, each of the following features that will be discussed may be, but are not required to be, used with any other feature or combination of features of the second aspect. For instance, any of the foregoing features described in relation to the first aspect may be applicable to the second aspect.

A third aspect includes a healthcare information exchange system for exchange of healthcare information between an electronic medical record (EMR) system and a dose fulfillment client for fulfillment of a dose order. The system includes a stream processing module in operative communication with an EMR system to receive a healthcare information data stream from the EMR system. The system further includes a staging table database in operative communication with the stream processing module for storage of a staging table populated with dose order metadata included in the healthcare information data stream. The staging table includes a plurality of dose order data fields populated with corresponding respective portions of the dose order metadata. The system further includes a transformation module operatively disposed between the staging table data base and a dose fulfillment client. The transformation module is operative to identify the dose fulfillment client for use in fulfillment of the dose order and transform the dose order metadata into a predefined format corresponding to the dose fulfillment client. Specifically, the predefined format defines dose order data fields and corresponding dose order metadata formats associated with the dose fulfillment client.

A number of feature refinements and additional features are applicable to the third aspect. These feature refinements and additional features may be used individually or in any combination. As such, each of the following features that will be discussed may be, but are not required to be, used with any other feature or combination of features of the third aspect. For instance, any of the foregoing features described in relation to the first aspect may be applicable to the third aspect.

BRIEF DESCRIPTION OF THE DRAWINGS

FIG. 13 is an embodiment of an interface for display of dose orders processed by a healthcare information exchange system.

FIGS. 14-16 depict a sequence of interfaces related to an embodiment of exception handling of a dose order with processing errors in relation to the exchange of data related to the dose order.

FIG. 17 is an embodiment of an interface for management of a transformation of healthcare information in a healthcare information exchange system.

FIG. 18 is an embodiment of an interface for a platform interface module depicting standardization of an EMR message into an intermediate standardized format.

DETAILED DESCRIPTION

Figure 1:
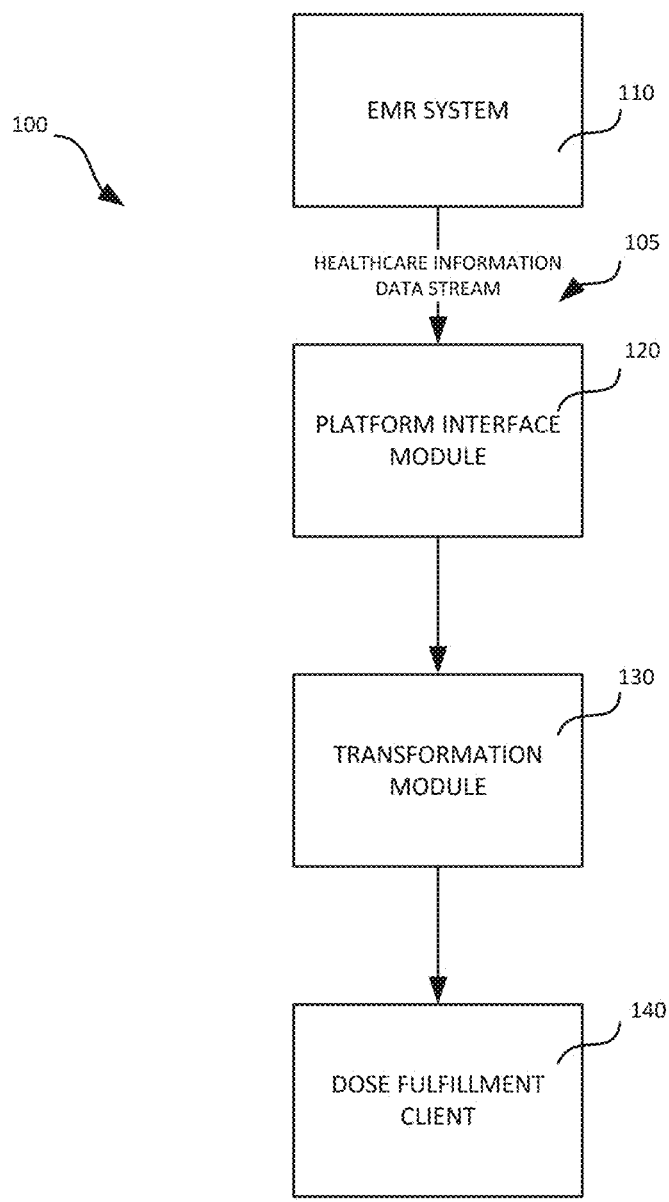
FIG. 1 is a schematic view of an embodiment of a system for facilitating exchange of healthcare information.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

FIG. 1 schematically depicts an embodiment of a system 100 for automated exchange of healthcare information. The system 100 may include an EMR system 110 that is in operative communication with a platform interface module 120. In this regard, the EMR system 110 may provide a healthcare information data stream 105 to the platform interface module 120. While a single EMR system 110 is shown in FIG. 1, it may be appreciated that a plurality of EMR systems 110 may be in operative communication with the platform interface module 120. The EMR systems 110 may correspond to different EMR systems 110 at a given facility or EMR systems 110 from a plurality of facilities. In any regard, the platform interface module 120 may be in operative communication with a transformation module 130. The transformation module 130 may in turn be in operative communication with a dose fulfillment client 140. As discussed in greater detail below, the transformation module 130 may be in operative communication with a plurality of dose fulfillment clients 140. As such, the transformation module 130 may include a dose routing module and/or perform dose routing functions in relation to dose orders received at the transformation module 130.

In this regard, the system 100 in FIG. 1 may be operative to facilitate automated data exchange between independent healthcare information systems. For example, the EMR system 110 and the dose fulfillment client 140 may each correspond to independent healthcare information systems and/or products. As described above, the EMR system 110 and the fulfillment client 140 may use unrelated or incompatible data formats. In turn, the platform interface module 120 and transformation module 130 may act upon the health information data stream 105 to transform the data from the form received from the EMR system 110 such that the healthcare information (e.g., comprising dose order data) may be exchanged between the EMR system 110 in the dose fulfillment client 140. Specifically, the data may be exchanged between the EMR system 110 and the dose fulfillment client 140 in an automated manner that avoids the requirement for human intervention with respect to the exchange of the healthcare information. In this regard and as described above, the automation of the exchange of information between the EMR system 110 and the dose fulfillment client 140 provided according to the disclosure presented herein may assist in reduction of errors and/or delays associated with human involvement with the healthcare information data stream 105 as it passes from the EMR system 110 to the dose fulfillment client 140.

The EMR system 110 may comprise a hospital information system (HIS). Accordingly, the healthcare information data stream 105 may comprise information regarding dose orders to be prepared by the dose of fulfillment client 140. However, the healthcare information data stream 105 may also include other healthcare information that is unrelated to dose orders or preparation of dose orders. For example, in the case of an HIS, the healthcare information data stream 105 may include patient related data (e.g., admission/discharge data), hospital management data (e.g., resource availability, scheduling, etc.), billing and accounting data, or other ancillary data unrelated to dose orders or the preparation of dose orders.

The healthcare information data stream 105 may be provided in a number of different formats. Furthermore, a given one platform interface module 120 may interface with a plurality of different ERM systems 110 each potentially providing healthcare information data streams 105 in differing formats. In an embodiment, the healthcare information data stream 105 may comprise a Health Level 7 (HL7) format. The HL7 format refers to set of loosely standardized conventions for the transfer of clinical and administration data between HISs. Despite the loose standardization of conventions provided by HL7 messages, the exchange of healthcare information between various independent healthcare systems employing HL7 formatting is not seamless. In this regard, different systems may utilize different lexicons, conventions, semantics, or other different standards within the HL7 format such that the exchange of information between two systems utilizing an HL7 format may still require intervention to allow for data exchange between systems.

Accordingly, the platform interface module 120 may receive the healthcare information data stream 105 from the EMR system 110 regardless of the nature of the format used (e.g., regardless of variations in HL7 formats). For instance, different specific EMR systems 110 (e.g., different HISs) may utilized varying HL7 formats, all of which may be received by the platform interface module 120. As will be discussed in greater detail below, the platform interface module 120 may be operative to identify and/or parse dose orders from the healthcare information data stream 105. The platform interface module 120 may in turn store the dose order records identified and parsed from the healthcare information data stream 105 in an a standardized intermediate format. For example, the standardized intermediate format may comprise a staging table for each respective dose order for which dose order metadata is parsed from the healthcare information data stream 105. In turn, the parsed dose order metadata may be used to populate fields of the staging table that correspond to dose order data fields from the healthcare information data stream 105.

It should be noted that the standardized intermediate format (i.e., the staging table) may standardized relative to different HL7 formats used by different HL7 providers. That is, if first HL7 provider provides a dose order with identical constituent ingredients as a second HL7 provider, the portions of the HL7 messages corresponding to the identical constituent ingredients for the doses may still differ based on differing usage of the HL7 format by the first and second providers to describe the identical constituent ingredients. However, the platform interface module 120 may standardize the differing portions of the HL7 messages regarding the constituent ingredients for the identical orders such that the constituent ingredients for the orders would appear identical in the standardized intermediate format. Furthermore, patient data, dose administration data, or other data related to the dose may be provided in different formats corresponding to different uses of the HL7 format. However, this data may also be standardized in the standardized intermediate format. In this regard, the staging table comprising the standardized intermediate format may standardize HL7 messages received in different healthcare data streams 105.

Figure 18:
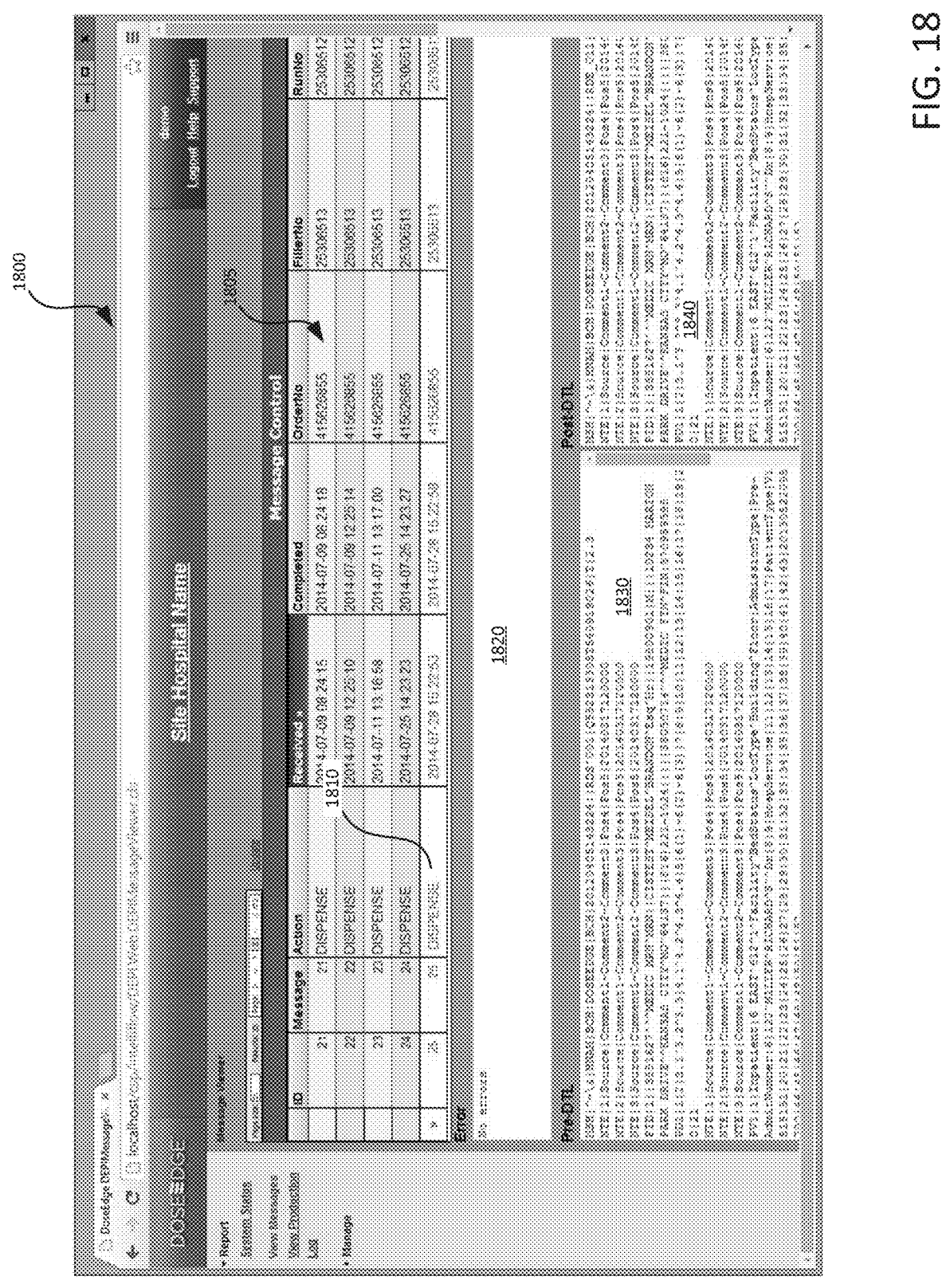

The generation of a standardized intermediate format is illustrated in FIG. 18 which depicts a user interface 1800 and may display a listing 1805 of receive dose orders. A user may be able to select a selected one 1810 of the dose orders from the listing 1805 of dose orders. Upon selection of the selected one 1810, corresponding information regarding the selected dose order 1810 may be displayed in an error pane 1820, a pre-standardization pane 1830, and a post-standardization pane 1840. In this regard, the error pane 1820 may provide information to a user regarding errors (e.g., parsing errors, identification errors, or other errors that may occur with respect to receipt of the dose order from an EMR system 110). Furthermore, the pre-standardization pane 1830 may display the dose order record as received from the EMR system 110. In this regard, the pre-standardization pane 1830 may display a textual representation of an HL7 message received from the EMR system 110 prior to undergoing standardization for population of a staging table. The post-standardization pane 1840 may display the corresponding textual representation of the dose order after having been standardized into the standardized intermediate format. That is, the post standardization pane 1840 may provide a standardized version of the pre-standardized HL7 format displayed in the pre-standardization pane 1830. Accordingly, the user interface 1800 may allow a user to review errors related to a selected dose order 1810. Furthermore, a user may be operative to review pre-standardization and post-standardization formats side-by-side for a given dose order to facilitate review and or troubleshooting related to the dose order.

The use of a standardized intermediate format may be particularly beneficial in the context of multiple healthcare data stream providers (e.g., multiple EMR systems 110 that may include, for example, HISs, PISs, POEs, or other healthcare information data stream 105 sources) and multiple dose fulfillment clients 140. For instance, rather than having to develop specific transformation logic for all possible combinations of EMR systems 110 and all dose fulfillment clients 140, the system 100 may provide a more modular approach. That is, as new EMR systems 110 are added to the system 100, a parsing module (described in greater detail below) may be provided to format the healthcare information data stream 105 into the standardized intermediate format for storage in a staging table. In turn, all existing dose fulfillment clients 140 may receive information as a transformation module 130 may be capable of transforming the standardized intermediate format into each dose fulfillment client 140 specific format. Further still, as different dose fulfillment clients 140 are added to the system that require unique input formats, rather than having to develop transformation logic for each potential EMR system 110, transformation logic relative to the standardized intermediate format may be generated. Accordingly, the standardized intermediate format allows for improved, modular development as additional components to which data is to be exchanged are added to the system 100.

The transformation module 130 may be operative to access the data regarding dose orders from the staging table maintained at the platform interface module 120. The transformation module 130 may be operative to transform the accessed data in the standardized intermediate format regarding the dose orders from the standardized intermediate format of the staging table into a specific format association with a dose fulfillment client. In this regard, the client-specific format may correspond to a unique input format associated with and/or required by a dose fulfillment client 140. In this regard, the unique input format for a given dose fulfillment client 140 may have input fields corresponding to dose order data fields of the staging table. In this regard, the transformation module 130 may map dose order data fields to corresponding input fields for the unique input format for a given dose fulfillment client 140. Furthermore, the transformation client 130 may translate dose order metadata from a first format stored in the staging table into a target format associated with the unique input format for a given dose fulfillment client 140. In this regard, the transformation module 130 may be operative to apply a transformation that is specific to a dose fulfillment client 140 to dose order data stored in the staging table based on a dose fulfillment client 140 that is identified to be used to fulfill the corresponding dose order.

As such, data regarding a dose order may be provided to a dose fulfillment client 140 in a format associated with a unique input format associated with the dose fulfillment client 140 such that the dose order data may be automatically provided to the dose fulfillment client 140 for use by the dose fulfillment client 140 in fulfillment of the dose corresponding to the dose order data. As will be appreciated from the further discussion below, the dose fulfillment client 140 may comprise any one or more of a number of different types of dose fulfillment clients that may be utilized in the fulfillment of a dose associated with a dose order. For example, the dose fulfillment client 140 may comprise any one or more of a pharmacy workflow management application for management of manual preparation of the dose, a total parenteral nutrition (TPN) client for processing in connection with and/or preparation (e.g., automated preparation) of a TPN dose order, an automated syringe filler, a dose dispensation cabinet with pre-stocked doses that may be allocated based on received dose order data to fulfill a dose, etc.

As will also be appreciated from the discussion below, the platform interface module 120 and transformation module 130 may each include hardware and/or software that comprise each respective module. Furthermore, the platform interface module 120 and the transformation client 130 may be collectively provided as a single module. That is, each module may comprise hardware and/or software for execution of functionality described below in relation to each respective one of the platform interface module 120 and/or transformation module 130. For example, the respective modules may individually or collectively comprise one or more processors in operative communication with a memory device that stores non-transitory machine-readable data that may be used to specifically configure the one or more processor for execution of functionality related to the modules as described below. In this regard, the respective modules may also comprise the memory device that stores non-transitory machine-readable data structure (e.g., such as a hard drive, flash drive, memory module, or other appropriate physical electronic memory) for storage of the non-transitory machine-readable data used for specific configuration of the one or more processors.

Figure 2:
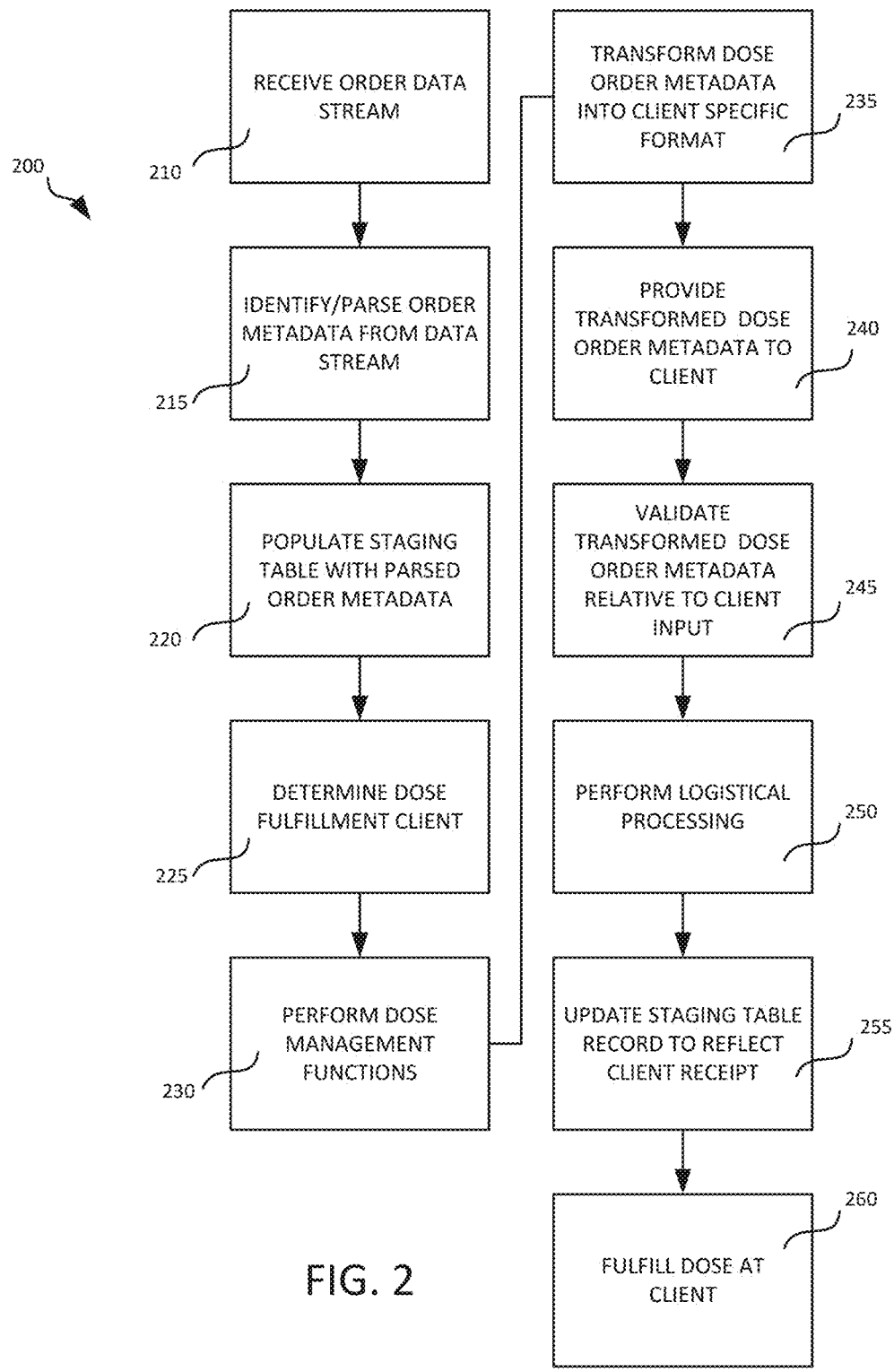
FIG. 2 is a flowchart depicting an embodiment of a method for exchange of healthcare information.

With further reference to FIG. 2, an embodiment of a method 200 for automated exchange of healthcare information between an EMR system 110 and a dose fulfillment client 140 is shown as a flowchart. While the method 200 is described herein in connection with the system 100 of FIG. 1, it will further be appreciated that the method 200 may be performed in connection with any other embodiment presented below. Furthermore, while the method 200 is depicted in the form of a sequential flow chart with specific discrete operations in a particular order, it is contemplated that the steps of the method discussed below may be performed in any order (or concurrently) unless otherwise specified. Also, further embodiments of the method are contemplated wherein some steps may be omitted. That is, all steps of the process need not be performed in each embodiment.

The method 200 may include receiving 210 a dose order data stream 105 (e.g., such as a health information data stream 105 comprising one or more dose orders therein). As may be appreciated, the receiving 210 may include transmission of the dose order data stream from the EMR system 110. In this regard, the dose order data stream may be sent upon initiation from the EMR system 110 (i.e., "pushed" from the EMR system 110) and/or be sent upon request by the platform interface module 120 (i.e., "pulled" from the EMR system 110). The method 200 may also include identifying/parsing 215 dose order metadata from the dose order data stream. In this regard, the identifying/parsing 215 may include analyzing the dose order data stream 105 to identify individual dose orders from the data stream 105. For example and as described above, the data stream 105 may include a plurality of dose orders and/or data that is unrelated to dose orders at all. In turn, the identifying may include delineating individual dose orders from the data stream 105. As such, the identifying may include recognition of data in a specific format indicative of a dose order. Additionally or alternatively, the data stream 105 may include express delineators to assist in identifying individual ones of the dose orders in the data stream 105. Additionally, dose order metadata may be parsed from the data stream 105 in regard an individual dose order. In this regard, the parsing may include locating one or more specific dose order data fields and corresponding dose order metadata related to the data fields. In turn, the dose order data fields and dose order metadata related thereto may be used in populating a dose order data field. In addition, standardization of the dose order metadata may be performed such that the staging table comprising the dose order data fields may include standardized dose order metadata (i.e., in a standardized intermediate format).

Any one or more of a plurality of dose order data fields may be included in the data stream 105 and, in turn, in a corresponding staging table related to the identified/parsed dose order may be provided and/or generated. As an example, a predefined staging table may be provided that includes predefined data fields that relate to patient specific data, ingredients of the dose order, administration details for the dose order, or other appropriate data fields that relate to the dose order, the administration of the dose order, or a patient which the dose orders to be administered. That is, any data field relevant to the preparation and/or administration of the dose order may be contained in the data stream 105. The data provided in relation to such data fields may in turn be standardized into a corresponding data field in a staging table that may include predefined data fields to which the dose orders in the data stream 105 are standardized. Additionally or alternatively, a staging table with data fields corresponding to the fields of the dose order in the data stream 105 may be generated upon receipt of the data corresponding to the dose order.

In this later regard, the method may include populating 220 a staging table with the identified/parsed dose order data from the data stream 105. For example, the staging table may include data fields stored as a specific data structure corresponding to the standardized intermediate format. For instance, the standardized intermediate format may be defined by a database schema associated with dose orders. In this regard, to the extent dose order metadata for a given dose order data field is parsed with respect to a given one of the dose orders in the data stream 105, a corresponding staging table instance (e.g., a row in the table and/or a unique staging table entry or record) may be generated and appropriate respective data fields according to the standardized intermediate format may be populated 220 the corresponding dose order metadata identified/parsed 215 from the data stream 105. In turn, a staging table corresponding to each identified individual dose order may be generated and populated 220 with parsed dose order data. It may be appreciated that the individual staging tables regarding corresponding individual dose orders may be collectively stored in a database. In this regard, individual database files need not be generated for each individual dose order, but rather an identified staging table or portion of a larger staging table (e.g., a unique row or record) may be specifically related to a given dose order for specific identification relative thereto.

The method 200 may, as an option in at least some embodiments, include determining 225 a dose fulfillment client for use in preparation of a given dose order. For example, the dose order data contained in the data stream 105 for a given dose order or plurality of doses may include an express identification of a dose fulfillment client 140 for use in fulfillment of the corresponding dose order(s) (e.g., the healthcare information data system 105 may include an indication of the dose fulfillment client 140 for given a given dose order that originates as data provided by the EMR system 110). That is, the EMR system 110 may send data indicative of the desired dose fulfillment client 140 to be used to fulfill a particular dose order (e.g., by indicating dose fulfillment client type or by indicating a specific identity of a dose fulfillment client) that is contained in the healthcare data stream 105. In another example, a source of the data stream 105 may be identified, and the identity of the source of the data stream 105 may at least in part be used to determine the dose fulfillment client 140 to which the dose order is to be provided for fulfillment. For example, all dose orders received from a specific given source may be defined as being dose orders corresponding to a specific dose fulfillment client 140 for use in fulfillment of those specific dose orders from the specific source. Further still, the determination 225 of the dose fulfillment client 140 for a dose order may be based upon one or more portions of dose order data. For example, the dose order data may define a dose characteristic (e.g., an ingredient, ingredient amounts, ingredient types, etc.) that may be used to determine 225 dose fulfillment client 140 for use in fulfillment of the dose order. In this regard, logic may be established in accord with any of the foregoing examples to facilitate determination 225 of the dose fulfillment client 140 for a given dose order. For instance, the logic may be executed by a client router 128 (e.g., shown in FIG. 3 et seq.) that may be provided at the transformation module 130. In other contemplated embodiments, the client router 128 may be provided remotely from the transformation module 130 (e.g., at the platform interface module 120 and/or as a completely separate module).

Furthermore, the method 200 may, as an option in at least some embodiments, include performing 230 dose management functions with respect to the dose orders received and stored in corresponding staging tables. For example, the dose orders stored in corresponding staging tables may be reviewed, modified, prioritized, grouped, organized, or otherwise managed. It should be noted that the dose management functions that may be performed 230 may occur prior to receipt of dose order data at a dose fulfillment client 140 and/or upon receipt of dose order data at the dose fulfillment client 140. That is, the dose management functions may be performed by the platform interface module 120, the transformation module 130, and/or the dose fulfillment client 140. For instance, the dose management functions may be performed by a queue management and prioritization module 152, which may be located at the platform interface module 120 (e.g., as a standalone module and/or as a component of the client router 128 or transformation module 130), at a dose fulfillment client 140, and/or disposed between the platform interface module 120 and a dose fulfillment client 140.

The method 200 may further include transforming 235 dose order data from the standardized intermediate format (e.g., the staging table) into a specific format associated with a dose fulfillment client 140 (e.g., a unique input format for a given dose fulfillment client 140). As will be described in greater detail below, the transforming 235 may include mapping dose order data fields of the staging table to input fields for a unique input format of a given dose fulfillment client 140. Furthermore, dose order metadata for a given dose order stored in a dose order data field may be translated into a format associated with the unique input format of the given dose fulfillment client 140. In this regard, the transformation 235 may be at least in part depending upon the determination 225 of the dose fulfillment client for a given dose order as described above.

The method 200 may further include providing 240 the transformed dose order data to a dose fulfillment client 140. In this regard, the dose fulfillment client may request the transformed dose order data (e.g., pull the data from the platform interface 120 and/or transformation module 130) and/or the dose fulfillment client 140 may have the transformed dose order metadata transmitted thereto (e.g., the data may be pushed from the platform interface 120 and/or transformation module 130).

In any regard, the method 200 may include validating 245 the transformed dose order metadata relative to the unique input format for the dose fulfillment client 140 that receives or is to receive the dose order data. For instance, the validating 245 may include determining whether required dose fulfillment client input fields are present in the transformed dose order data. Furthermore, the validating 245 may include analyzing a portion of transformed dose order data to determine if a valid corresponding portion of data is available in the unique input format for the dose fulfillment client 140. In this regard, in the event the validating 245 is unsuccessful, an exception may be generated with respect to a dose order. In turn, the method 200 may include exemption processing to resolve an error associated with the validation 245. Examples of exception processing are provided below in greater detail.

The method 200 may also, as an option in at least some embodiments, include performing 250 logistical processing with respect to the dose orders. For example, the dose order data stream 105 may include order messages of differing types. For instance, dose order message types may relate to new dose orders, dose order change requests, dose order cancellation requests, or other appropriate dose order requests. That is, at least some of the dose order message types processed may require subsequent actions to be taken on a previously received dose order. Accordingly, in the event dose order data is processed and provided to a dose fulfillment client 140 and a subsequent dose order message is received that requires action be taken with respect to the dose order data provided to the dose fulfillment client 140, additional logistic processing may be performed 250. This may include analysis of prior dose orders to determine the state of the previous dose order (e.g. whether the dose order has yet been sent to the dose fulfillment client, whether the dose has been fulfilled, etc.). Additionally, the logistical processing may also include performing actions (e.g., modification, cancellation, etc.) of a prior dose order as required by a subsequently received dose order message. Furthermore, it may be appreciated that a dose order message may apply to a dose order that has been routed to a first dose fulfillment client 140, but upon the execution of the dose order message is to be recalled from the first dose fulfillment client 140 and provided to a second dose fulfillment client 140.

The method 200 may also include updating 255 a staging table to reflect receipt of a dose order at the dose fulfillment client 140. For instance, the updating 235 may include modifying a data field of the staging table associated with an indication of the dose order status to indicate the dose order record has been provided to and/or received by the dose fulfillment client 140.

The method 200 may further include fulfilling 260 a dose at the dose fulfillment client 140. The fulfilling 260 may include preparation of a dose corresponding to a dose order at the dose fulfillment client 140. The preparation may be a manual operation to prepare the dose order, an automated operation to fulfill the dose order, or a combination thereof. Further still, the fulfilling 260 may include making available a dose (e.g., a pre-prepared) to satisfy a dose order (e.g., such as providing instructions to a dose dispensation cabinet to make a prepared dose available for fulfillment of the dose order).

Figure 3:
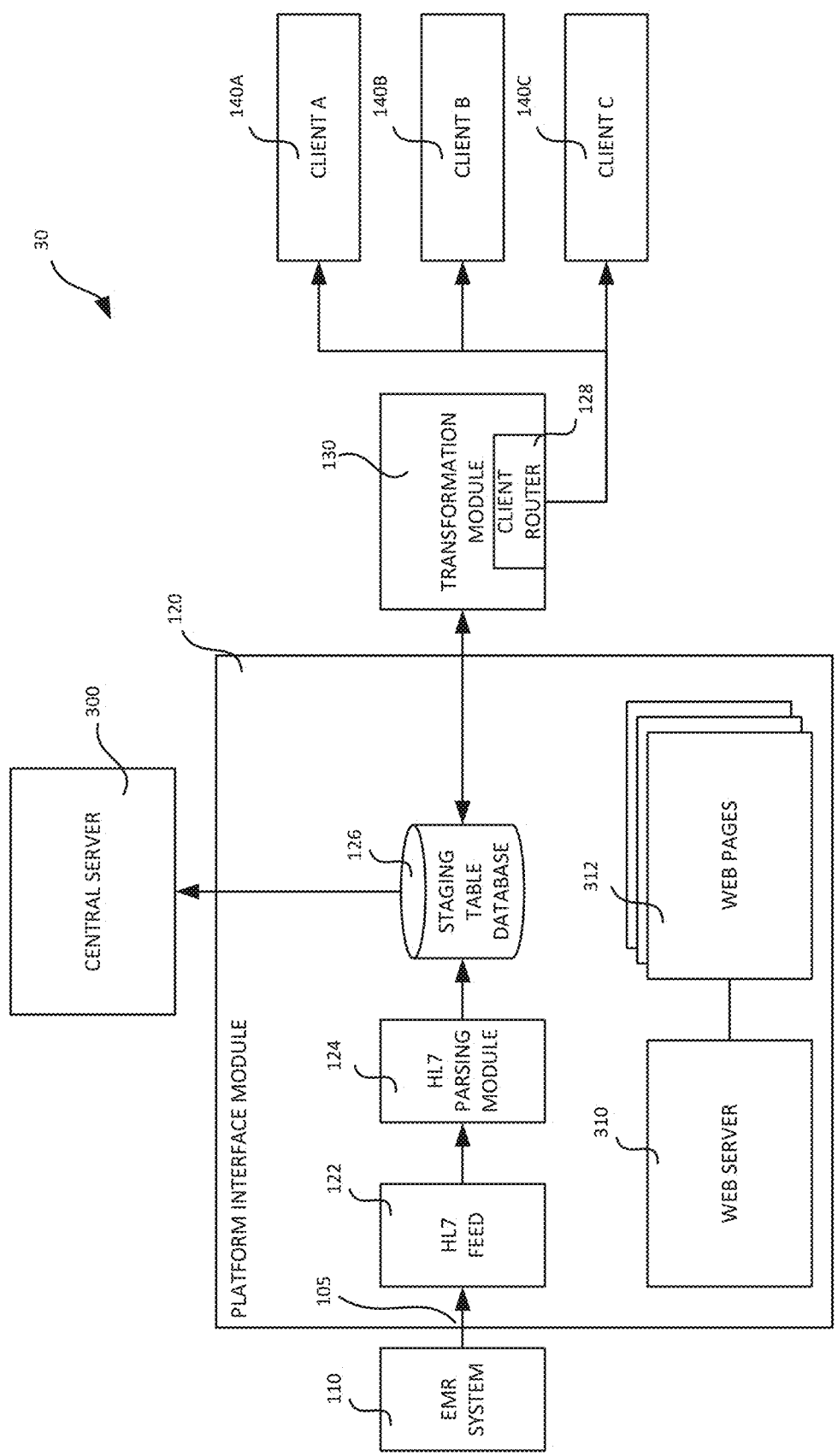
FIG. 3 is a schematic view of an embodiment of a system for facilitating exchange of healthcare information between an EMR system and a plurality of dose fulfillment clients.

With further reference to FIG. 3, a schematic depiction of an embodiment of a system 300 for automated healthcare exchange is depicted. The system 30 may include an EMR system 110 that provides a healthcare information data stream 105 in the form of an HL7 data feed to a HL7 data feed port 122 of the platform interface module 120. In turn, the HL7 data received at the HL7 data feed port 122 may be provided to an HL7 parsing module 124. In this regard, the HL7 parsing module 124 may identify/parse dose orders from the HL7 data feed received at the HL7 data feed port 122. As such, the HL7 parsing module 127 may comprise a stream processing module. The HL7 parsing module 124 may also determine if the dose order identified form the data stream 105 is to be processed by the exchange system 30. For instance, a dose may be processed by the system as described herein or may be diverted to a different dose handling system by the parsing module 124 based on the dose order identified.

In any regard and as described above, a staging table may be populated for a dose order identified/parsed from the data stream 105. The staging table may be a predefined data structure that is populated with identified/parsed data from the data stream 105. In turn, the dose order data may be used to populate fields in the staging table corresponding to dose order data fields with dose order metadata from the data stream 105. In turn, the staging table regarding the dose order may be stored in a staging table database 126.

The staging table database 126 may be in operative communication with a central server 300 that is disposed remotely from the platform interface module 120. In this regard, data regarding the dose orders stored as staging tables in the staging table database 126 may be provided to the central server 300. The central server 300 may receive dose order data from a plurality of platform interface modules 120 (e.g., from different healthcare facilities implementing platform interface module 120). The central server 300 may facilitate backup and/or data aggregation services in relation to the dose order data.

The staging table database 126 may be in operative communication with a transformation module 130. In this regard, the transformation module 130 may be operative to retrieve a staging table from the staging table database for transformation of the dose order data contained therein. Additionally, the transformation module 130 may include a client router 128. In turn, the client router 128 be operative to provide transformed dose order data (e.g., in a unique input format for a given dose fulfillment client 140) to an appropriate dose fulfillment client 140. While shown as a common module, the client router 128 may also be provided separately from the transformation module 130 (e.g., as a standalone module or as a module provided in connection with the platform interface module 120).

As described briefly above, various methods for determining an appropriate dose fulfillment client 140 to which the dose order is to be directed may be applied by the client router 128. In this regard, the client router 128 may employ any one or more of the approaches described above to determine an appropriate dose fulfillment client 140 to which the transformed dose order data may be provided. In this regard, shown in FIG. 3, a plurality of clients 140A, 140B, and 140C may be provided in operative communication with the client router 128. In turn, the client router 128 may provide an appropriate one of the fulfillment clients 140A, 140B, 140C with the transformed dose order data such that the appropriate dose fulfillment client 140 may be used to fulfill the dose corresponding to the dose order.

As may be appreciated, the determination of the appropriate dose fulfillment client 140 to which the dose order will be provided may affect the transformation of the dose order by the transformation module 130. In this regard, the transformation module 130 may comprise the client router 128 as depicted or may be in bidirectional communication with the client router 128 such that the transformation module 130 and client router 128 may collectively act upon the data in a staging table to determine the dose fulfillment client 140 to which the dose order will be prepared such that the identity of the determined dose fulfillment client 140 may at least in part affect the transformation applied to the dose order data by the transformation module 130. For instance, upon identification of an appropriate dose fulfillment client 140 by the client router 128, a unique input format for the identified dose fulfillment client 140 may used to transform the dose order data from the staging table.

In other embodiments (e.g., such as that depicted in FIG. 5 discussed in greater detail below), the transformation module 130 of the embodiment of the system 30 may be provided at the platform interface module 120. Furthermore and as addressed in greater detail below in relation to other embodiments, the client router 128 may be located the platform interface module 120. In this regard, the fulfillment clients 140A, 140B, and 140C may each be operative to receive transformed dose order data for use in fulfillment of the dose corresponding to the dose order. That is, in at least some embodiments, all processing regarding the dose order data for exchange with the dose fulfillment client 140 may occur at the platform interface module 120. However, in other embodiments, such as those described below, different functionality with respect to the transformation module 130 and/or client router 128 may be provided in a distributed manner remotely from the platform interface module 120.

The platform interface module 120 may also include a web server 310 that provides for remote access to the functionality provided by the platform interface module 120. For example, the web server 310 may maintain and/or execute one or more web pages 312 corresponding to the various modules and/or functionality provided by the platform interface module 120. In turn, the web pages 312 may facilitate functionality in connection with the platform interface module 120 and/or modules provided comprising the platform interface module. For instance, various settings, parameters, or other administrative functions may be performed with respect to platform interface module 120. Such functionality may be facilitated by way of the web pages 312 that are accessed by way the web server 310.

Figure 4:
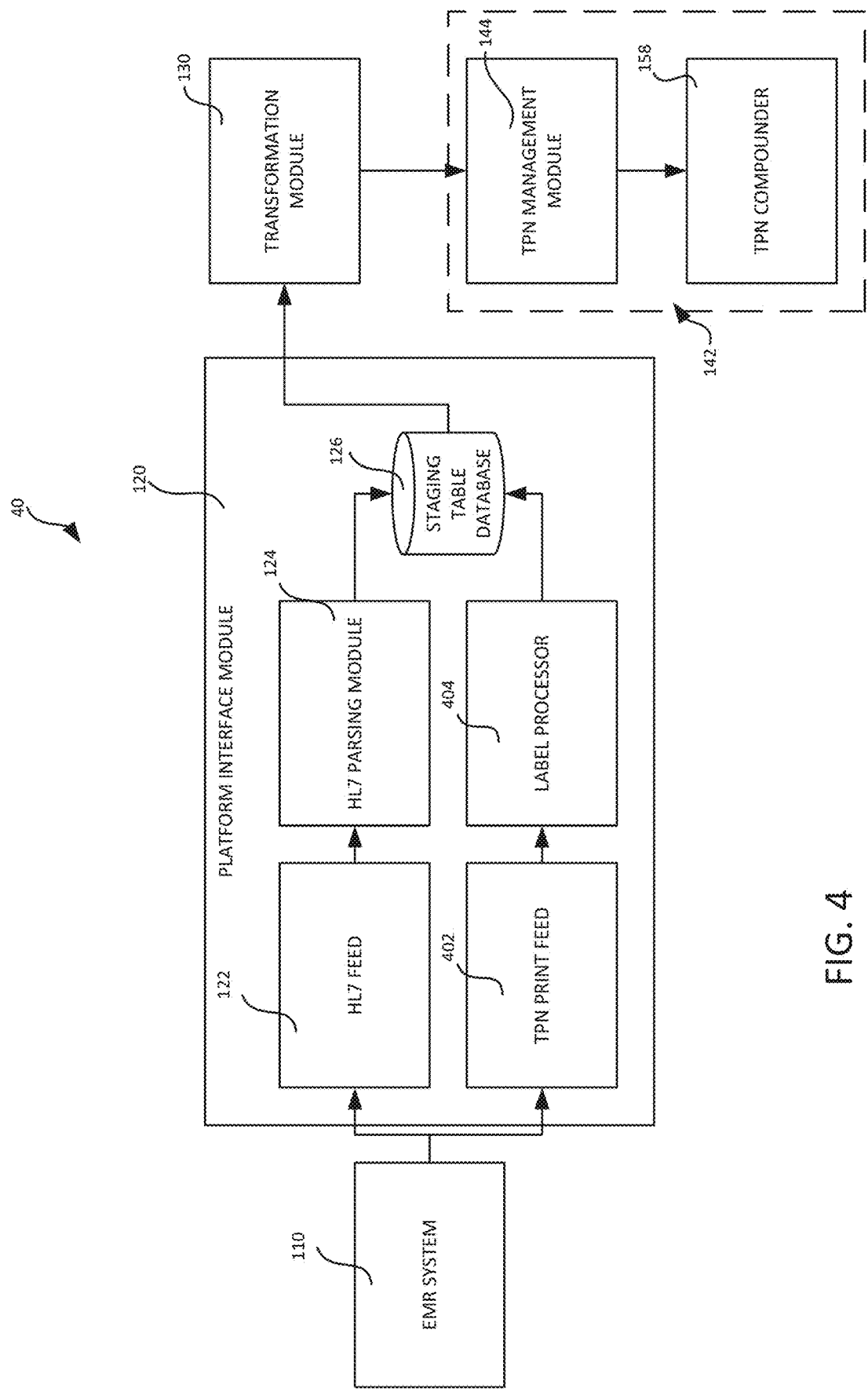
FIG. 4 is a schematic view of an embodiment of a system for facilitating exchange of healthcare information between an EMR system and a dose fulfillment client for fulfillment of total parenteral nutrition dose.

With further reference to FIG. 4, another embodiment of a system 40 for automated exchange of healthcare information is depicted. The system 40 may be particularly useful in the context of fulfillment of total parenteral nutrition (TPN) dose orders received from the EMR system 110. The system of FIG. 4 may be configured to receive TPN dose orders from the EMR system 110 in a plurality formats. For example, the platform interface module 120 may include an HL7 data feed port 122 to which HL7 format messages from the EMR system 110 may be routed and parsed as described above in connection with FIG. 3. The platform interface module 120 may also include a TPN print data feed 402 to which print feed data messages from the EMR system 110 may be routed. In this regard, the platform interface module 120 may facilitate both the capability to process HL7 format messages as well as print feed messages received from the EMR system 110. Examples of HL7 message formats that may be processed may include, but are not limited to, HL7 messages originating from EMR systems provided by Cerner Corporation, Epic Systems Corporation, Meditech, Omnicell, Inc., or others. Furthermore, examples of supported print feed formats may include, but are not limited to, Zebra programming language provide by Zebra Technologies, DataMax format provided by DataMax-O'Neil, Intermec format provided by Intermec, Inc., portable document format (PDF) provided by Adobe Systems, plain text format, etc.

In this regard, HL7 messages may be provided from the HL7 data feed port 122 to an HL7 parsing module 124 as described above in relation to FIG. 3. Additionally, the TPN print data feed 402 may provide print feed messages to a label processor 404 of the platform interface module 120. In any regard, the HL7 parsing module 124 and/or the label processor 404 may provide individual dose order metadata in relation to corresponding dose order data fields for storage as a staging table in a staging table database 126.

In the example provided in FIG. 4, the platform interface module 126 may be in direct communication with a TPN fulfillment client 142. In this regard, the TPN fulfillment client 142 may be a dose fulfillment client 140 capable of fulfilling TPN dose orders. For instance, the TPN fulfillment client 142 may include a TPN management module 144. The TPN management module 144 may facilitate dose order calculation and management. For instance, the TPN management module 144 may comprise ABACUS Calculation Software provided by Baxter Healthcare Corporation of Deerfield, IL. In any regard, the TPN fulfillment client 142 may provide further processing in relation TPN dose orders in connection with the fulfillment of TPN dose orders (e.g., calculations related to ingredient interactions, etc.). The TPN management module 144 may be in further communication with a TPN compounder 158. The TPN compounder 158 may be operative to autonomously prepare a dose corresponding to a TPN order. In this regard, in an embodiment, the dose fulfillment client 140 may comprise the TPN fulfillment client 142 that collectively includes the TPN management module 144 and/or the TPN compounder 158. That is, the transformation module 130 may communicate directly to the TPN management module 144 or the TPN compounder 158. As such, the unique input format utilized by the transformation module 130 may correspond to the TPN management module 144 or the TPN compounder 158.

In this regard, and as depicted in FIG. 4, a transformation module 130 may be provided in operative communication with the staging table database 126 and the TPN client 142. In this regard, the transformation module 130 may access the staging table database 126 to retrieve dose order data in the standardized intermediate format of the staging table that is transformed by the transformation module 130 into a unique input format for use with the TPN client 142. In this regard, the system 40 of FIG. 4 may not include a client router 128. For instance, the platform interface module 120 may be utilized in a dedicated manner to receive only TPN dose orders from the EMR system 110. In this regard, the TPN client 142 may access the staging table database 126 to retrieve all staging tables contained therein for transformation by the transformation module 130 into the unique input format associated with the TPN management module 144. That is, the platform interface module 120 may be used in a dose context-specific application wherein only a single type of dose orders to be fulfilled by a given dose fulfillment client 140 (e.g., the TPN fulfillment client 142) are processed by the platform interface module 120.

Figure 5:
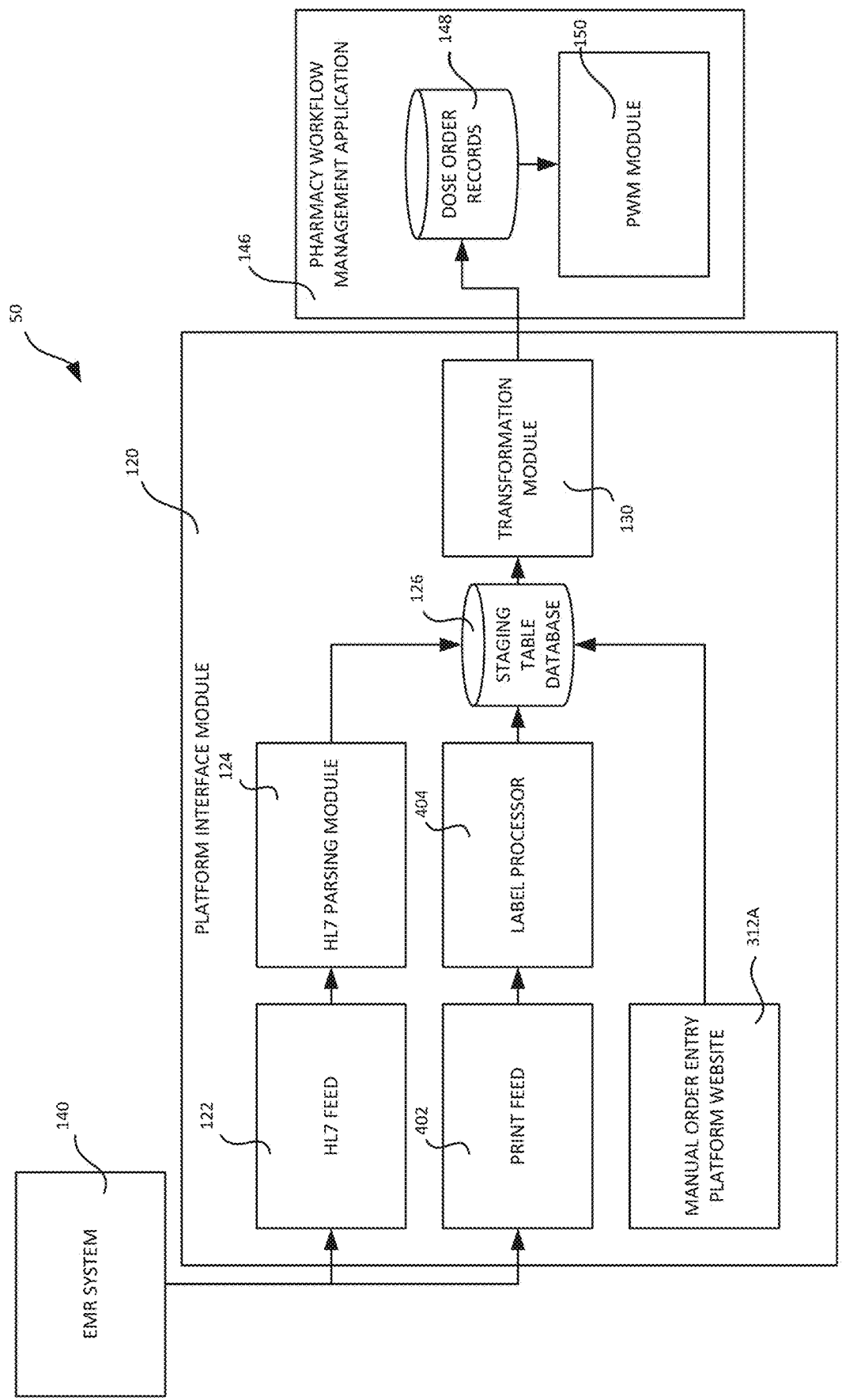
FIG. 5 is a schematic view of an embodiment of a system for facilitating exchange of healthcare information between an EMR system and a pharmacy workflow management application for fulfillment of a dose order.

FIG. 5 depicts another embodiment of a system 50 for exchange of healthcare information. The system 50 may also receive HL7 format messages as well as print feed messages from an EMR system 110 that are processed by an HL7 data feed port 122 and a print feed port 402, respectively, as described above in relation to FIG. 4. As described above, data messages may be routed to an appropriate one of an HL7 parsing module 124 or a label processor 404 for generation of a staging table stored in the staging table database 126 for corresponding receive dose orders. FIG. 5 further includes a manual order entry website 312A (e.g., as provided in websites 312 access by web server 310 of FIG. 3). In this regard, user may access the platform interface module 120 directly using the manual order entry website 312A to generate a dose order directly at the platform interface module 120 that are stored in a staging table in the staging table database 126.

In the embodiment of the system 50 depicted in FIG. 5, platform interface module 120 may be in operative communication with a pharmacy workflow management application 146. In this regard, the pharmacy workflow management application 146 may be the only dose fulfillment client 140 with which the platform interface module 120 is in operative communication. In this regard, as depicted in FIG. 5, the transformation module 130 may be provided with platform interface module 120 for transformation of dose order data stored in staging tables of the staging table database 126 into a unique input format associated with the pharmacy workflow management application 146. Upon receipt of the transformed dose order data, the data may be stored in the dose order record database 148 of the pharmacy workflow management application 146. In turn, the dose orders may be provided to a pharmacy workflow management module 150. The pharmacy workflow management module 150 may allow for manual preparation of a dose order by a pharmacy technician or the like. For example, embodiments of a pharmacy workflow management application 146 is described in the commonly assigned U.S. provisional Application No. 62/057,906 filed on Sep. 30, 2014 entitled "MANAGEMENT OF MEDICATION PREPARATION WITH FORMULARY MANAGEMENT", the entirety of which is incorporated by reference herein, may be utilized to fulfill dose orders at the pharmacy workflow management application 146.

Figure 6:
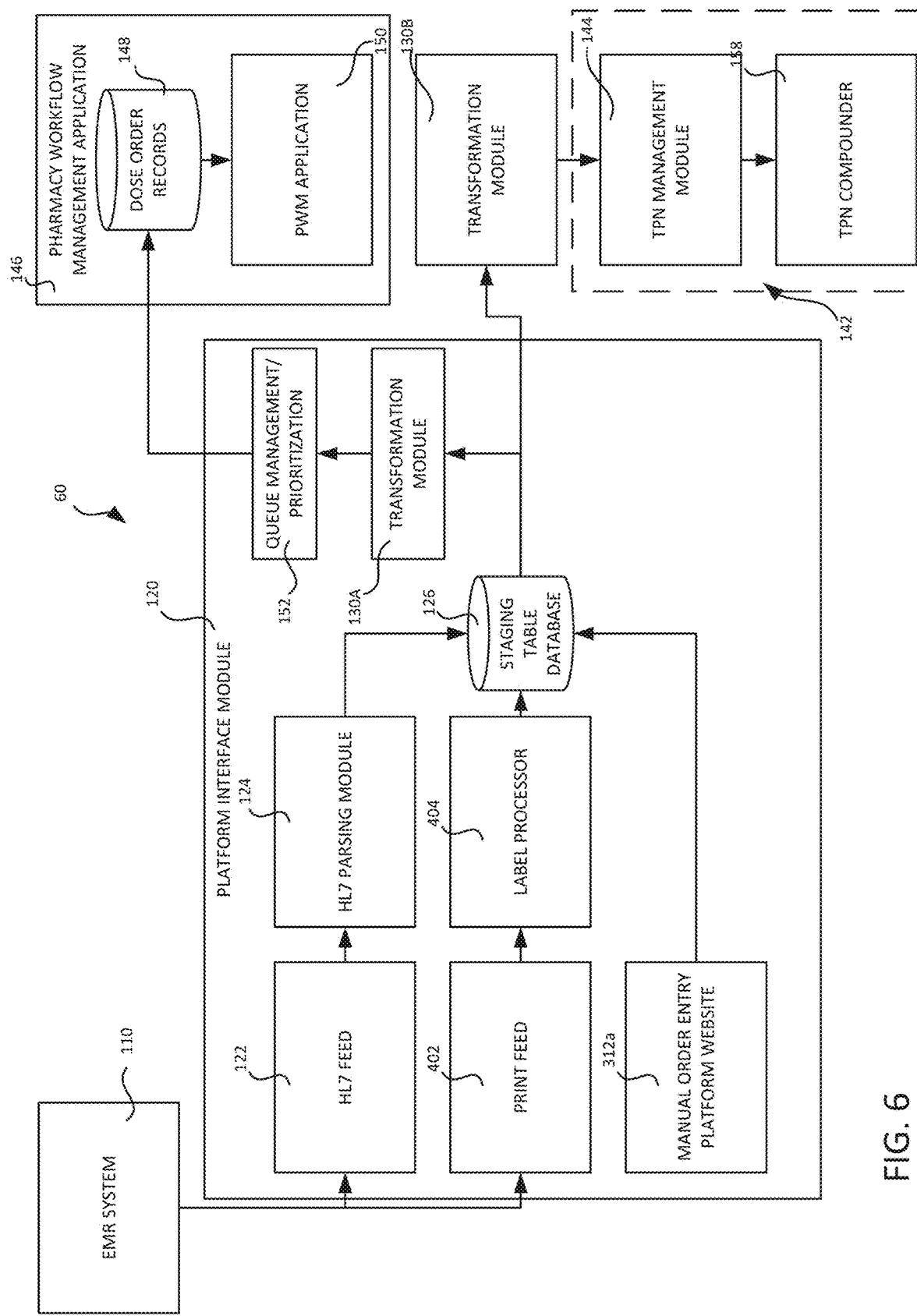
FIGS. 6-8 are schematic views of embodiments of a system for facilitating exchange of healthcare information between an EMR system and a plurality of dose fulfillment clients.

With further reference to FIG. 6 another embodiment of a system 60 for automated healthcare information exchange is depicted. The system 60 may receive dose order information from an EMR system 110 by way of an HL7 data feed port 122, a print data feed port 402, or by way of manual order entry from a manual order entry website 312A as described above in connection to FIG. 5. In this regard, dose order data may be received and used to populate corresponding staging tables that are stored in the staging table database 126.

The system 60 of FIG. 6 further includes a plurality of dose fulfillment clients 140. For instance, the platform interface module 120 is in operative communication with a pharmacy workflow management application 146 and a TPN fulfillment client 142. The system 60 of FIG. 6 may have a local transformation module 130A provided at the platform interface module 120. The local transformation module 130A may perform data transformation on dose order data that are provided to the pharmacy workflow management application 146. Additionally, a queue management and prioritization module 152 may be provided for management of dose orders corresponding to dose order data that are to be provided or that are provided to the pharmacy workflow management application 146.

Additionally, the TPN fulfillment client 142 may have associated therewith a remote transformation module 130B located remotely from the platform interface module 120 for transformation of dose order data locally with respect to the TPN fulfillment client 142 for dose order data corresponding to dose orders directed to the TPN fulfillment client 142. In this regard, the system 60 of FIG. 6 may have different transformation modules 130A and 130B for transformation of dose order data provided to the pharmacy workflow management application 146 and the TPN fulfillment client 142, respectively. Furthermore, a queue management and prioritization module 152 may be provided for at least a portion of the dose orders being directed to a given one of the dose fulfillment clients (e.g., the pharmacy workflow management application 146). The queue management and prioritization module 152 may be operative to manage dose orders prior to or after data transformation has occurred with respect thereto. Thus, while shown as residing between the transformation module 130 and the pharmacy workflow management application 146 in FIG. 6, one or more queue management and prioritization modules 152 may be provided elsewhere for management of dose order queues (e.g., at the staging table database 126, at the dose fulfillment client 140, etc.).

As described above briefly, the determination of the fulfillment client 140 to which the dose order data may be provided may occur in a number of manners. For example, each respective client may access the staging table database 126 and request dose order data that are flagged (e.g., include a data field indicative of) as being designated for the given dose fulfillment client 140 requesting the information. Furthermore, logic may be applied to the dose order data based on a number of different potential parameters to identify a dose fulfillment client 140 for use in fulfillment of a given dose order. In this regard, the fulfillment clients 140 may be provided dose order data for use in fulfillment of the dose order based on a data field in which the designated dose fulfillment client 140 is indicated as determined by application of the logic.

Figure 7:
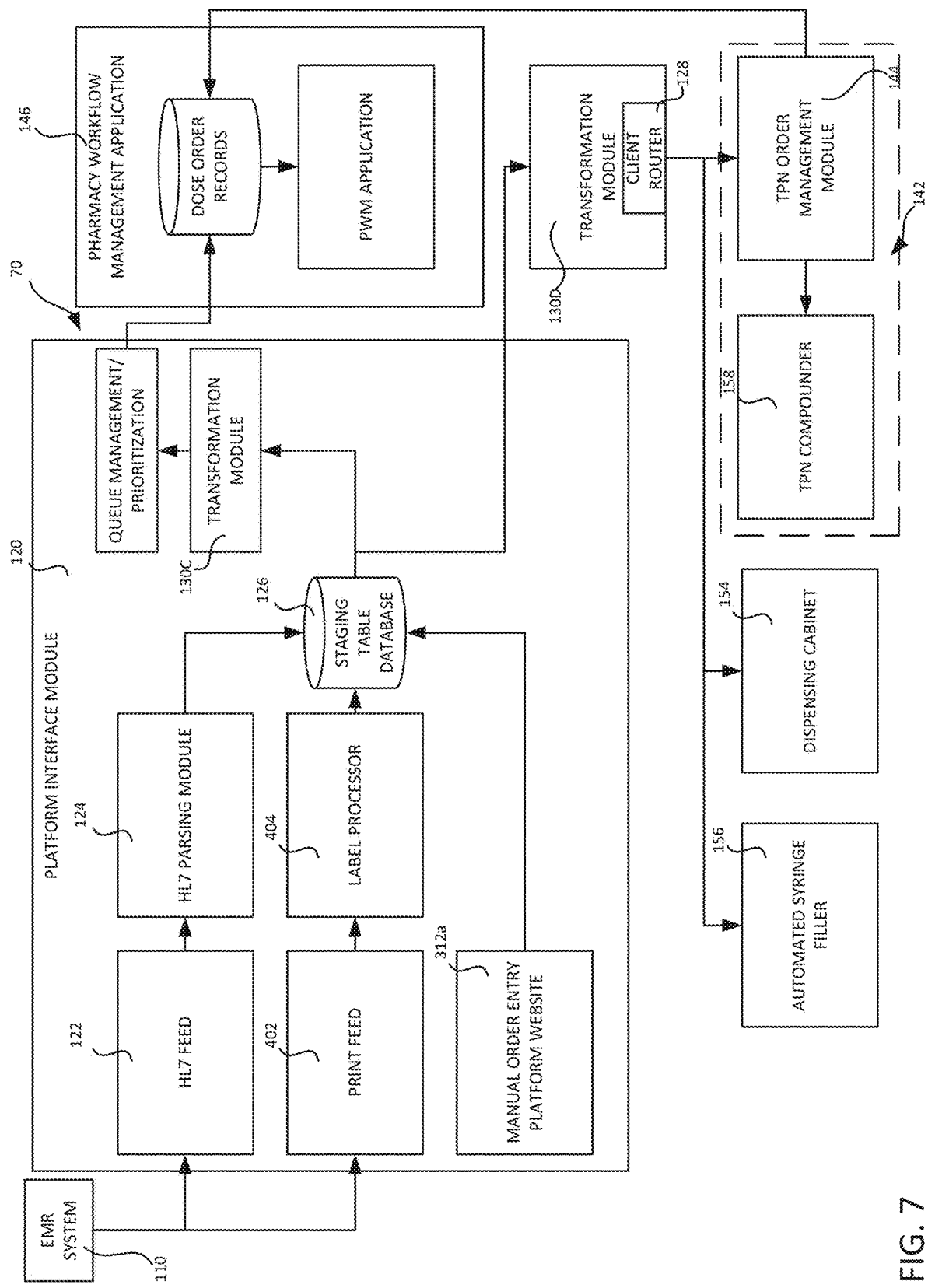

With further reference to FIG. 7, an embodiment of a system 70 for automated exchange of healthcare information is depicted. The system 70 may receive dose order data from an EMR system 110 as described above. The system 70 may also include a transformation module 130D that facilitates transformed data being provided to one or more of a plurality of dose fulfillment clients 140 (e.g., comprising the TPN client 142, a dispensing cabinet 154, or an automated syringe filler 156 in the depicted embodiment). The transformation module 130D may include a client router 128.

In this regard, the dose fulfillment clients 140 of the system 70 may include a pharmacy workflow management application 146, a TPN client 142, a dispensing cabinet 154 (e.g., an automated dose dispending cabinet), and/or an automated syringe filler 156. A portion of the dose orders from the staging table database 126 may be provided to the pharmacy workflow management application 146 by way of transformation module 130. Another portion of dose orders may be provided to the transformation module 130D. In turn, the client router 128 of the transformation module 130D may be operative to identify a dose fulfillment client 140 to which the dose order should be provided. As such, the client router 128 may apply any appropriate logic with respect to the dose order to determine the appropriate dose fulfillment client 140. For example, the client router 128 may identify and utilize a dose fulfillment client flag in the dose order has received from the EMR system to direct the dose order to an appropriate dose fulfillment client 140. Furthermore, the client router 128 may dynamically route the dose order to an appropriate fulfillment client 140 based on the dose order metadata contained by the dose order. Specifically, the client router 128 may be operative to determine whether the dose order is appropriate for automated preparation (e.g., by an automated syringe filler 156). In this regard, if the dose order is appropriate for automated preparation, the client router 128 may provide the dose order to an appropriate automated dose fulfillment client 140 (e.g., such as automated syringe filler 156). Further still, the client router 128 may be operative to identify if the dose order is appropriate for fulfillment by way of an automated dispensing cabinet 154.

As may be appreciated, it may be depended upon the specific dose fulfillment client 140 to which a dose order is provided as to the processing of the specific dose order data. For example, upon provision of dose orders to one of the pharmacy workflow management application 146 transformation module 130C that is provided locally to the platform module interface 120 may allow for transformation of the dose order data in the staging table database 126 into a unique input format corresponding to pharmacy workflow management application 146. Furthermore, the transformation module 130D may be provided (e.g., remotely from the platform interface module 120) for transformation of dose order data with respect to the TPN fulfillment client 142, dispending cabinet 154, or automated syringe filler 156. In this regard, the TPN fulfillment client 142 may include a TPN compounder 158 for compounding of the TPN dose order according to the dose order data received at the TPN client 142 and transformed by the transformation module 130D. Furthermore, the TPN order management module 144 may provide information to the pharmacy workflow management application 146. While shown as a direct connection, it is anticipated that the dose order data may be provided by way of the platform interface module 120 and/or transformation module 130C). Further still, the dose order data may be provided to both the pharmacy workflow management application 146 and the TPN fulfillment client 142 and an indication of a correlation between the dose order data provided to each respective dose fulfillment client 140, respectively.

Figure 8:
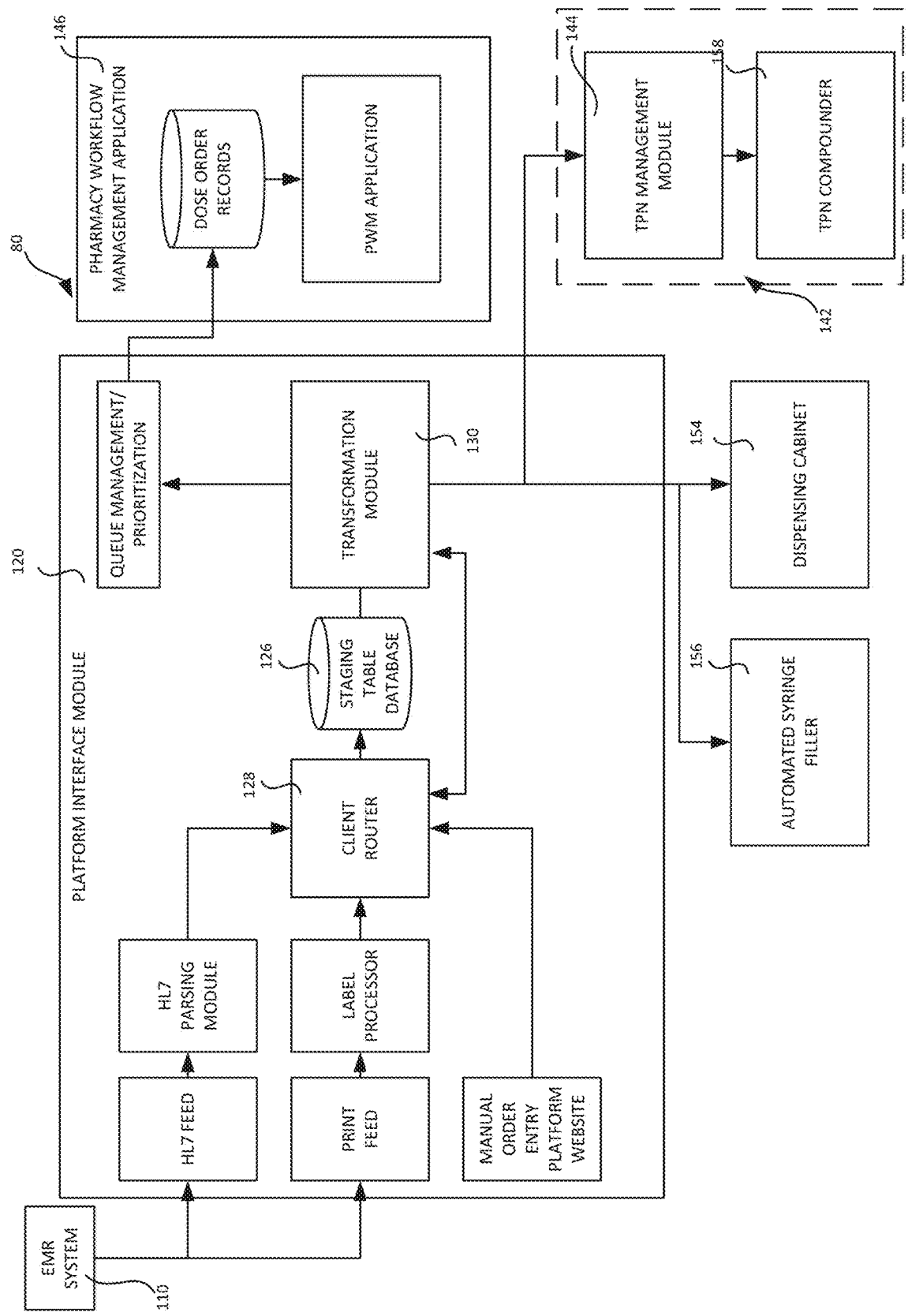

FIG. 8 further depicts a system 80 that, like the system 70 in FIG. 7 is in operative communication with a pharmacy workflow management application 146, a TPN client 142, a dispensing cabinet 154, and/or an automated syringe filler 156. However, unlike the system 70 in FIG. 7, the system 80 in FIG. 8 may include a single transformation module 130 provided at the platform interface module 120 for transformation of dose order data from the standardized intermediate format of the staging table stored in the staging table database 126 into a corresponding unique input format for a given dose fulfillment client 140. In this regard, the platform interface module 120 may include a client router 128 that is disposed between the staging table database 126 and the EMR system 110 or other means of order entry. In this regard, the client router 128 may be operative to apply logic to determine an appropriate one of the dose fulfillment clients 140 for use with each respective one of the dose orders. In this regard, the client router 128 may append information to the data in the staging table for a given dose order indicative of a dose fulfillment client 140 to which the dose order is to be provided. Further still, the client router 128 may be in operative communication with transformation module 130 to provide information regarding the dose fulfillment client 140 to which a dose order for a given staging table may be provided.

In any of the foregoing embodiments, the respective systems for automated transformation healthcare information may also facilitate logging with respect to actions taken relative to a dose order. The logging may include generating logs that reflect the actions taken on the dose order. The logs may be maintained for later review by human user (e.g., in the performance of an audit, troubleshooting, or the like). The logging may occur, and the logs may be stored, at different respective portions within the system. For example, the platform interface module 120 may perform logging to generate corresponding logs. Furthermore, the transformation module 130 (e.g., regardless of their specific location within the systems) may also perform logging to generate corresponding logs. In this regard, the logs may be maintained at different respective portions within the system. Additionally or alternatively, the logs may be transmitted within the system to a common location. For example, the platform interface module 120 may be in operative communication with transformation modules 130, or dose fulfillment clients 140 to receive logs there from regarding processing in relation to dose orders. In this regard, the logs for one or more portions of the system may be collectively stored at a given point in the system such as, for example, the platform interface module 120.

Figure 9:
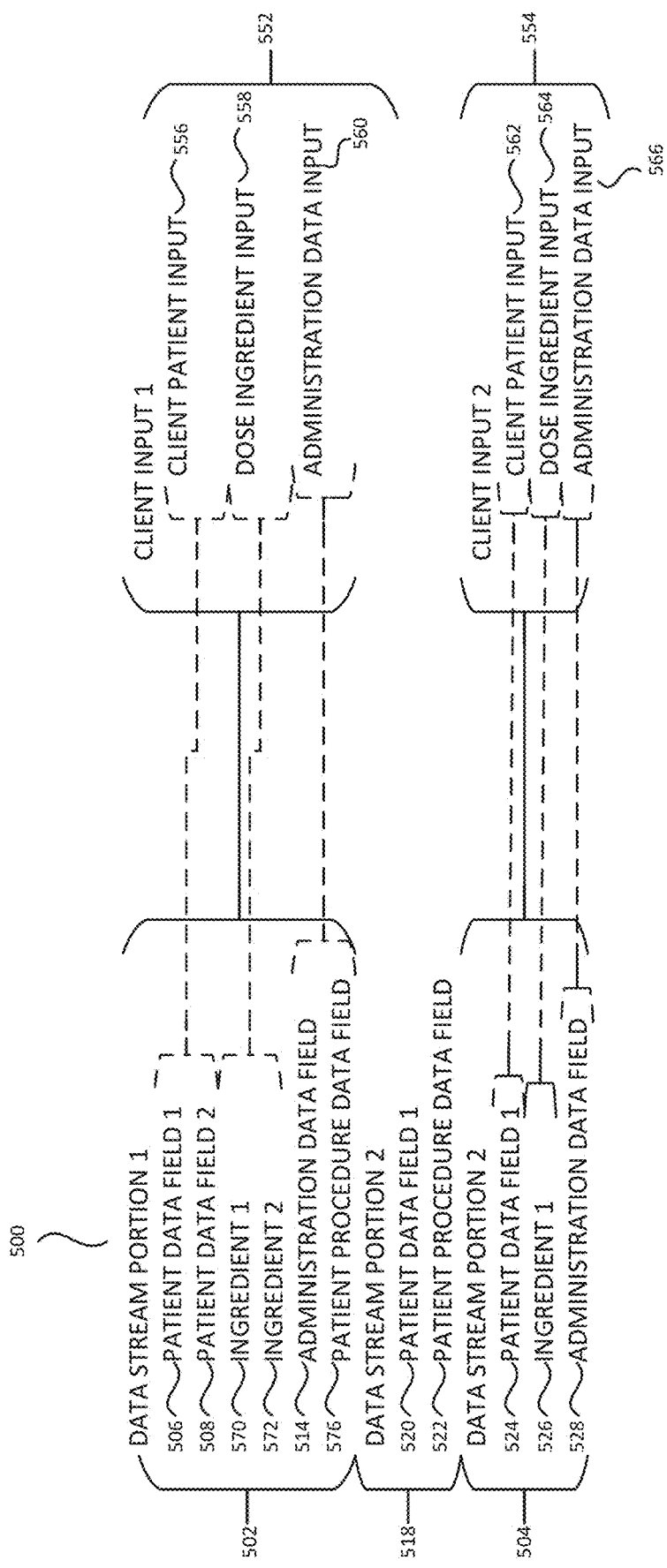
FIG. 9 is an embodiment of a textual representation of a mapping between a healthcare information data stream and an input format for a dose fulfillment client.

With further reference to FIG. 9, a representation of a data transformation performed by a transformation module 130 is shown. Specifically, FIG. 9 includes a textual representation of the data transformation in human perceivable form. FIG. 9 includes a representation of an embodiment of a date feed 500. As may be appreciated, the data feed 500 may be analyzed (e.g., by a parsing module of the platform interface module 120). The parsing may result in a dose order 502 and a dose order 504 being identified. As may be appreciated, a portion 518 of the data stream 500 may not correspond to a dose order.

Dose order 502 may be parsed such that a number of dose order data fields are recognized. Specifically, the dose order 502 may include a first patient data field 506, a second patient data field 508, a first ingredient field 510, a second ingredient field 512, an administration data field 514, and a patient procedure data field 516. Additional or fewer data fields may be present such that those presented are for demonstrative purposes only. The second dose order 504 may be parsed such that a first data patient field 524, a first ingredient field 526, and an administration data field 528 are identified. In this regard, the data for the first dose order 502 and the second dose order 504 may be stored in respective staging tables. As such, the textual representation of the first dose order 502 may correspond to the staging table for the first dose order 502 and the textual representation of the second dose order 504 may correspond to the staging table for the second dose order 504. While depicted textually in FIG. 9, it may be appreciated that the actual staging tables may be maintained in a different format such as an XML format, a SQL database format, or other appropriate format.

In any regard, the transformation module 130 may be operative to map data fields from the staging tables 502 and 504 to corresponding fields in unique input formats for one or more dose fulfillment clients 140. For instance, a first input 552 may be generated that corresponds to the staging table for the first order 502. As may be appreciated, the first input 552 may have defined fields according to a unique input format for a specific dose fulfillment client 140. As such, appropriate ones of the data fields in the staging table 502 may be mapped to fields in the first input 552. Specifically, the first patient data field 506 and the second patient data field 508 may be mapped to the client patient info field 556 of the first input 552. In this regard, it may be appreciated the multiple data fields from the staging table 502 may be mapped to a single field in the first input 552. In this regard, the data from the multiple fields (e.g., the first patient data field 506 and the second patient data field 508) of the staging table 502 may be aggregated or reformatted for inclusion in the client patient input 556. Furthermore, a portion of the data contained in one of the first patient data field 506 or second patient data field 508 may be omitted.

Further examples of the matching between data fields in the staging tables 502, 504 and the first and second input 552, 554 provided in FIG. 9. Specifically, the first ingredient field 510 and the second ingredient field 512 may be mapped to a dose ingredient input 558 of the first input 552. Furthermore, the administration data field 514 of the first staging table 502 may be mapped to the administration data input 560 of the first input 552. Of note, not all data field of the first staging table 502 may be mapped to the first input 522. For example patient procedure data field 516 may be irrelevant for the dose order, and therefore not have a corresponding input field of the first input 552 to which the patient procedure data field 516 is mapped. Furthermore, while the first staging table 502 demonstrates that multiple data fields from the staging table 502 may be mapped to a single info field in the first input 552, it may also be appreciated that one to one correspondence may be provided such as in the case of the second dose order 504. In this regard, the first patient data field 524 of the second dose order 504 may be mapped to the client patient input 562 of the second input 554. Furthermore, the first ingredient field 526 may be mapped to the dose ingredient input 564, and the administration data field 528 may be mapped to the administration data input 566. Furthermore, it should be noted that portion 518 of the data stream not corresponding to a dose order may not be mapped to any client input. That is, at least one platform interface module 120 or transformation module 130 may recognize the portion 518 is not corresponding to the dose order such that no corresponding input is generated or mapped to the portion 518.

Figure 17:
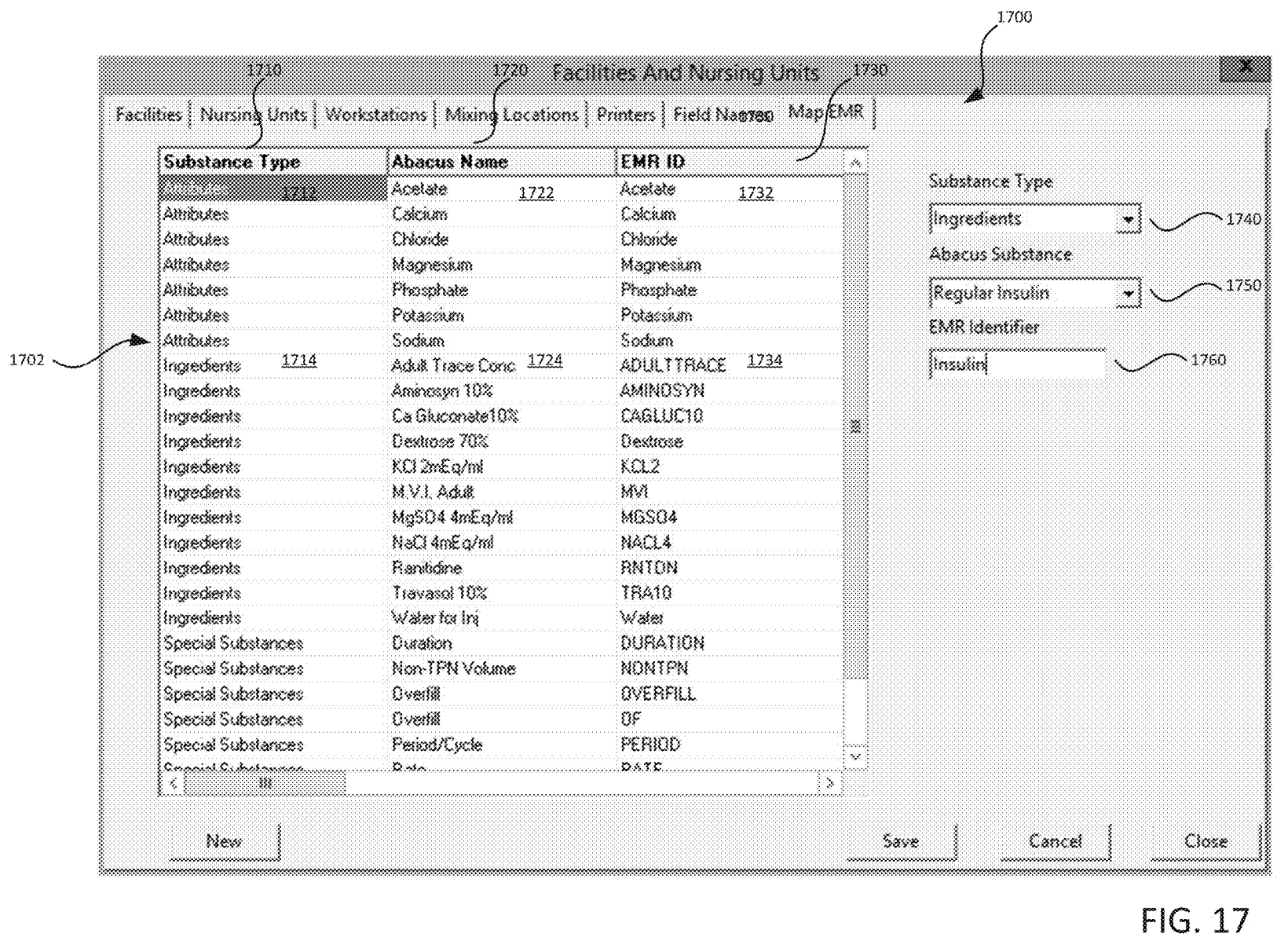

In addition to the mapping of data fields corresponding to dose orders to client input fields, the transformation module 130 may also perform translation with respect to the data contained in each respective field such that the data within each respective field may be translated into a format or form expected by the client in a given client info field. For instance, with further reference to FIG. 17, a user interface 1700 that includes representations of potential translations to be performed by the transformation module 130 is provided. The user interface 1700 may include a type listing 1710, a client form listing 1720, and an EMR form listing 1730 provided in a table 1702. In this regard, the table 1702 may include a plurality of listings (e.g., arranged by type 1710) for translation from a EMR form 1730 to a client form 1720. As may be appreciated, some listings may provide identical forms for the EMR form 1730 and the client form 1720. For example, the form corresponding to listing 1712 for "Acetate" may be the same for the EMR form 1732 and the client form 1722. However, as may be appreciated from the listing 1702, other forms may differ between the EMR form 1730 and the client form 1720. For example, listing 1714 may have a EMR form of "ADULTTRACE" and a client form 1724 of "Adult Trace Conc." Accordingly, should the EMR form 1734 for listing 1714 appear in a data field for a staging table, the data may be translated to the client form 1724 by the transformation module 130. In this regard, the user interface 1700 may also include a type filter 1740 and a client form filter 1750 that may be used to narrow the results presented in the table 1702. Furthermore, upon selection of a given listing within the table 1702, the EMR form 1730 for a given listing may be modified using the EMR form input 1760. For instance, upon selection of a listing from the table 1702 for a given portion of data, the EMR form 1730 may be modified for the listing using the EMR form input 1760. Furthermore, listings may be added or removed from the listing 1702 by the user. In this regard, it may be appreciated that the user may be able to maintain the definitions provided in the listing 1702 regarding translations to be applied by the transformation module 103 using the user interface 1700. In this regard, the user interface 1700 may be provided by a webpage 312 of the platform interface module 120 and/or may be provided by a dose fulfillment client 140 that comprises a transformation module 130 as described above.

Figure 10:
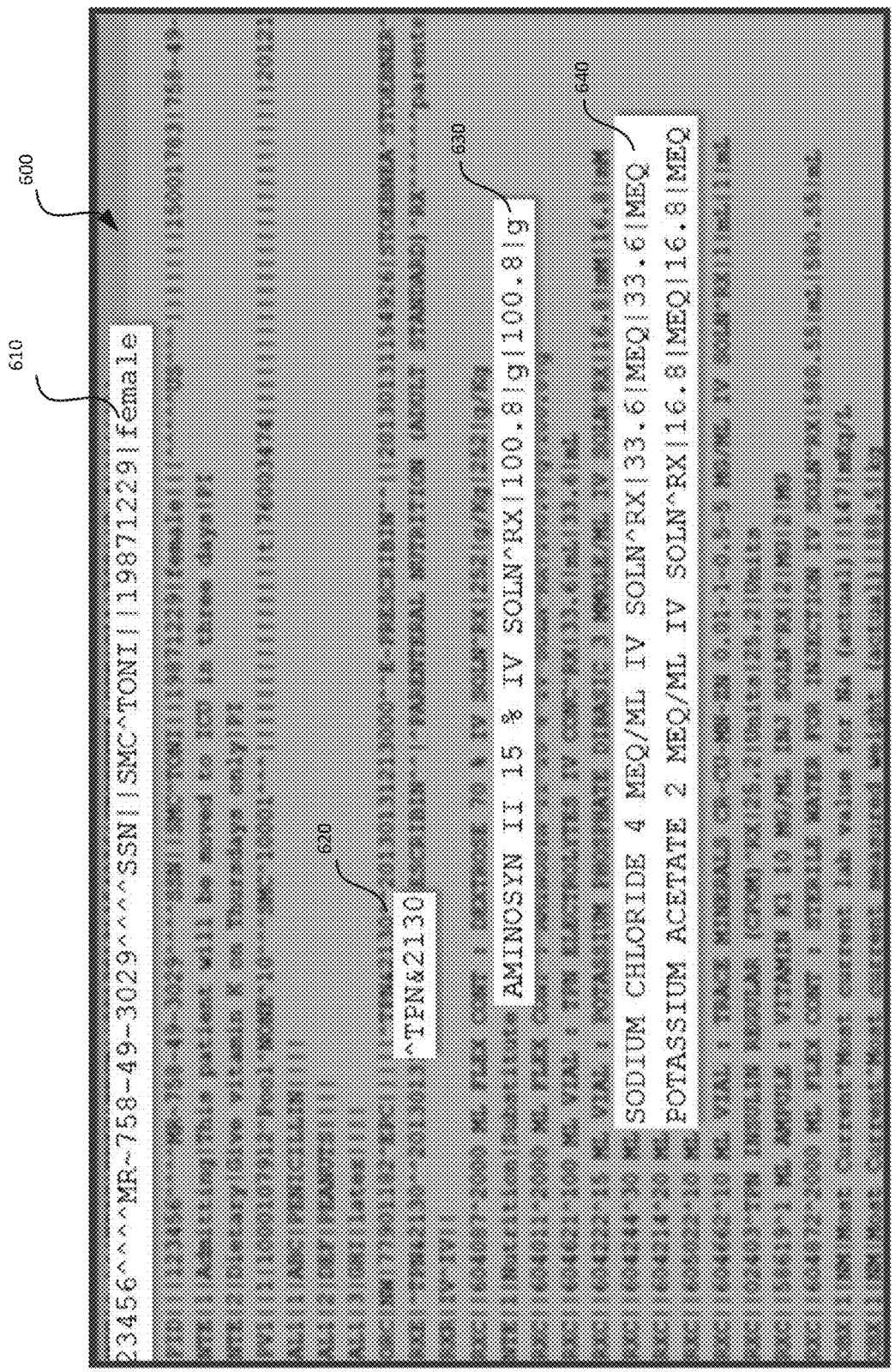
FIG. 10 is an embodiment of a human readable representation of an EMR system message comprising a dose order.
Figure 11:
FIG. 11 is an embodiment of a human readable representation of the operation of a transformation module executing relative to the EMR system message of FIG. 10.
Figure 12:
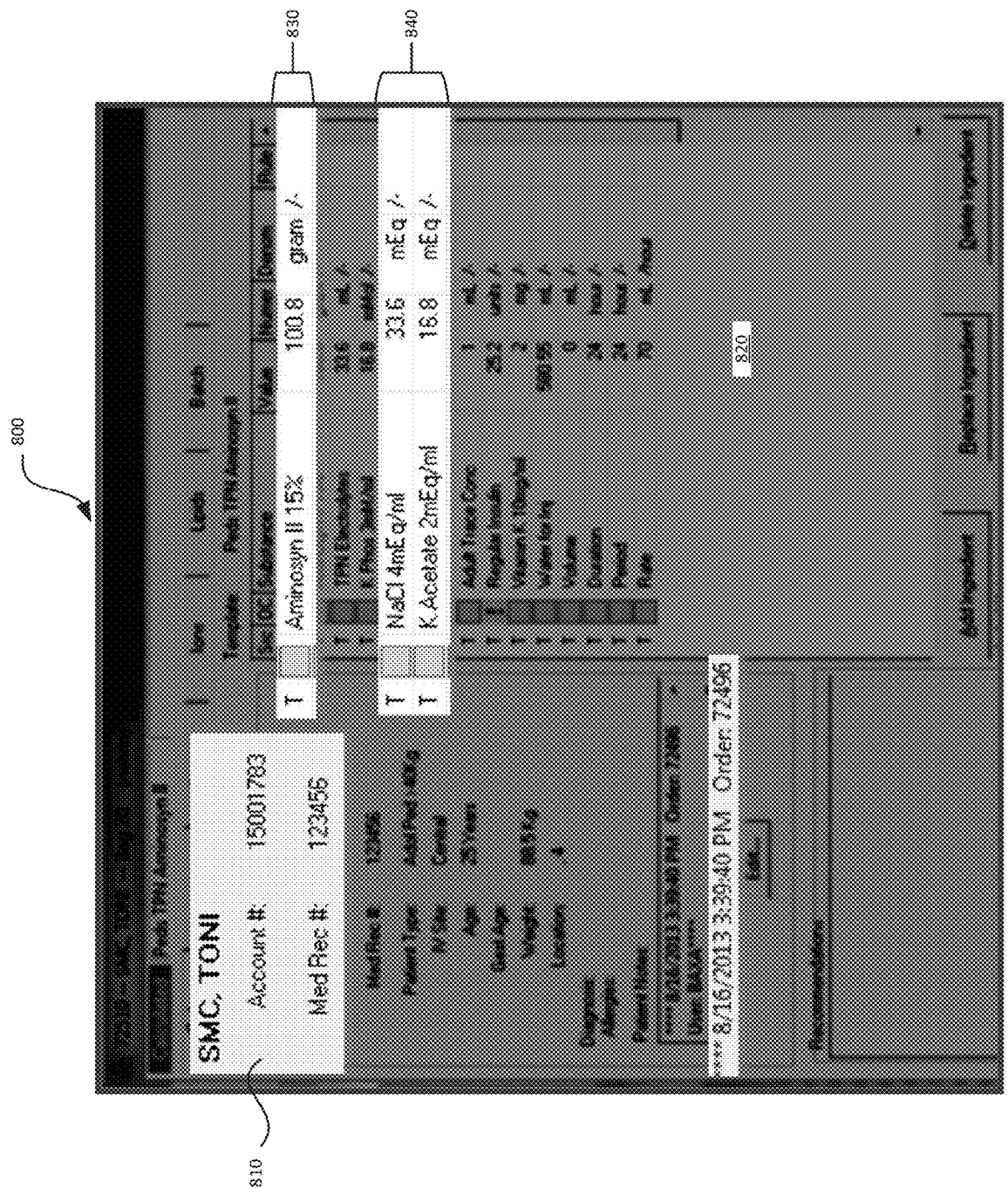
FIG. 12 is an embodiment of a dose fulfillment client interface corresponding to the dose order of the EMR system message of FIG. 10.

With further reference to FIGS. 10-12, an example of the processing of a dose order from an EMR system 110 to a dose fulfillment client 140 is depicted. Specifically, FIG. 10 depicts a textual representation of the data stream 600 from which the dose order is identified. In turn, FIG. 11 presents a textual representation of a log maintained by a transformation module 130 when acting upon the identified dose order from the data stream 600. FIG. 12 represents a user interface 800 of a dose fulfillment client 140 that is received the dose order. In this regard, the textual representation of the data stream 600 may include a plurality of data fields. For example, highlighted data fields corresponding to a patient data field 610, a dose order type field 620, a macro ingredients detail field 630, and a micro ingredients detail field 640 that are identified for a given dose order from the data stream 600. In this regard, the metadata for each corresponding field may be stored in a staging table. For example, the metadata found within the patient data field 610 may be used to populate one or more fields in a staging table related to the patient. Specifically, the name "TONI SMC," a gender "female," a date of birth "19871229," and an EMR number "123456" may be identified in the patient data field 610. Furthermore, an identifier indicating the dose order is a TPN order may be identified from the dose order type field 620. Furthermore, a macro ingredient 630 "AMINOSYN II 15% IV SOLN^RX|100.8|g|100.8|g" for the dose order 630 may be contained within the macro ingredient data field 630. Furthermore, to micro ingredients "SODIUM CHLORIDE 4 MEQ/ML IV SOLN^RX|33.6| MEQ| 33.6|MEQ" and "POTASSIUM ACETATE 2 MEQ/ML IV SOLN^RX|16.8|MEQ|16.8|MEQ" may be identified in the micro ingredients detail field 640.

With further reference to the log 700 generated by the transformation module 130, it may be appreciated that the transformation module 130 may convert the patient data field 610 into an input for creation of a patient in the dose fulfillment client 140 (e.g., in this case an ABACUS Calculation Software application) at line 710. Furthermore, the dose order type field 620 may be used to create an input for the creation of an order at the dose fulfillment client 140 at line 720. In turn, the order for the dose fulfillment client 140 may be populated with inputs corresponding to the macro ingredient detail 630 and the micro ingredient detail 640 such that those data fields are represented in the order input data 734 the dose fulfillment client 140. As may be appreciated, the macro ingredient detail field in the micro ingredient detail field 630 and 640 may be transformed into a format associated with unique input format associated with the dose fulfillment client 140. In this regard, the input fields 630' and 640' corresponding to the macro ingredient detail field 630 and the micro ingredient detail field 640 may contain data in a translated format. In turn, the inputs to the dose fulfillment client 140 reflected in the log 700 may be used to provide inputs to the dose fulfillment client 140.

In turn, FIG. 12 displays a user interface 800 of the dose fulfillment client 140 after receiving the commands reflected in the log 700. As may be appreciated, patient information file 10 may be presented with information corresponding to the data contained in the patient data field 610. Specifically, the patient name, the EMR number, an age based upon the date of birth provided in the patient data field 610, or other information may be provided in the patient information field 810. Furthermore, in ingredient listing 820 of the dose fulfillment client 140 may be provided. As may be appreciated, the macro ingredient 830 listed in the ingredient listing 820 corresponds to the data contained in the macro ingredient data field 630. The micro ingredients 840 listed in the ingredient listing 820 correspond to the data contained in the micro ingredient data field 840. As may be appreciated, the form of the ingredients 830 and 840 may be different from that contained in the data fields 630 and 640, thus reflecting the translation performed by the transformation module 130.

Figure 13:
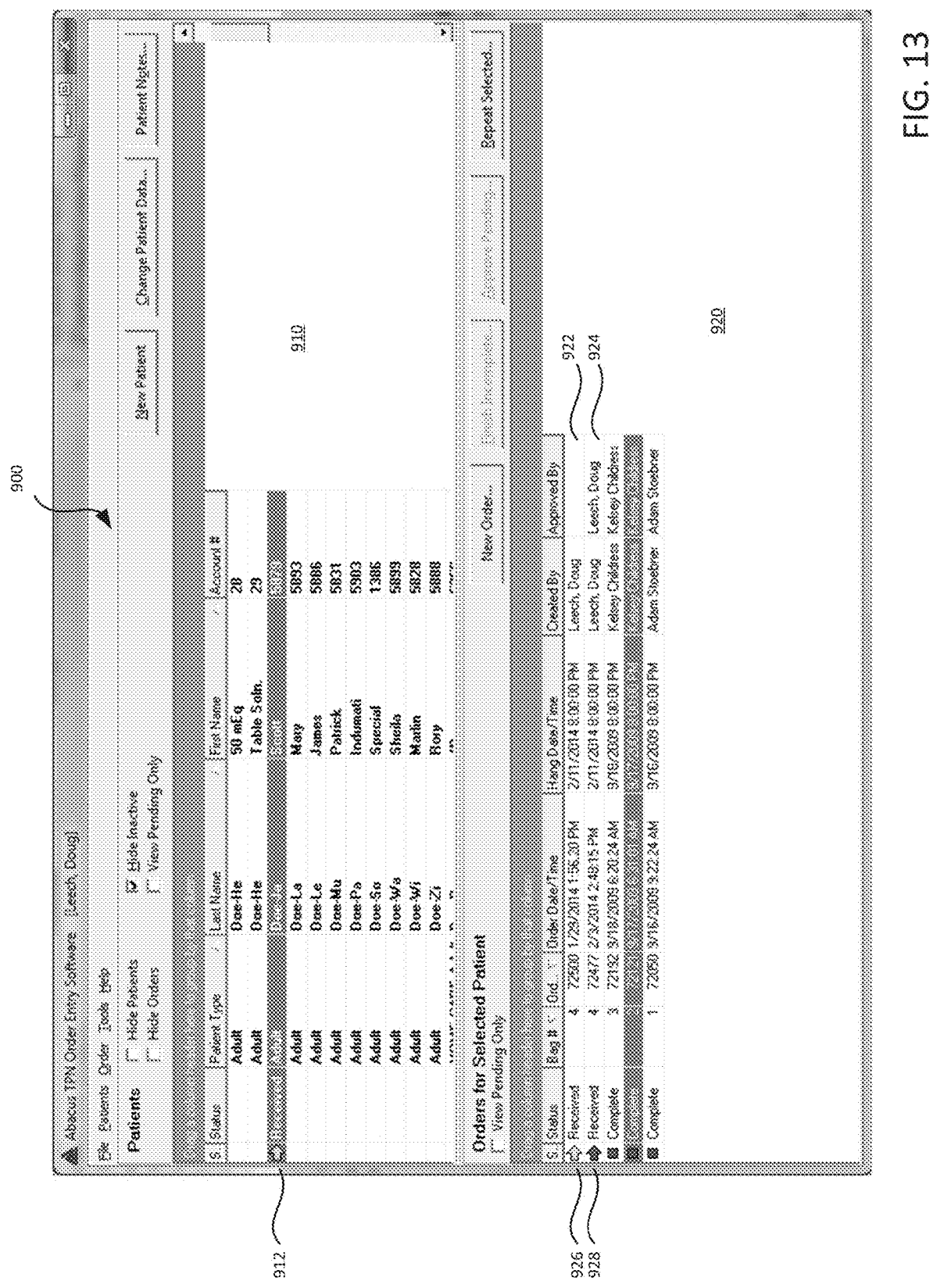

With further reference to FIG. 13, the user interface 900 for a dose fulfillment client 140 is depicted. The user interface 900 may include a patient listing 910. The patient listing 910 may list patients for which dose orders are pending. Upon receipt of a dose order from a transformation module 130, the dose fulfillment client 140 may update the patient listing 910 with the status indicator 912 to indicate that the dose order has been received. In this regard, the user interface 900 may further include an order listing field 920. The order listing field 920 may list complete and pending dose orders for a given patient selected from the patient listing 910. As may be appreciated, a first pending order 922 and second pending order 924 may be indicated as having been received by the dose fulfillment client 140. Status indicators for the received pending doses 922 and 924 may be provided. Specifically, a first status indicator 926 may be provided to indicate that no exceptions were generated in connection with the processing of the first pending order 922 by the platform interface module 120 and/or transformation module 130. In this regard, the first status indicator 926 may indicate the first pending dose order 922 is ready to be fulfilled by the dose fulfillment client 140.

The second status indicator 928 provided with the second pending dose order 924 may indicate that an exception was generated during the processing of the second pending dose order 924. Upon selection of the second pending dose 924, a dose detail screen 950 depicted in FIG. 14 may provided to the user. The dose detail screen 950 may include a patient information field 810 is described above in connection with FIG. 12. Furthermore, the dose detail screen 950 may include an ingredient listing 820 as described above in connection with FIG. 12. The dose detail screen 950 may also include an exception field 960 that may list exceptions identified during the processing of the dose order by the platform interface module 120 and/or transformation module 130. For example, exceptions may be identified with respect to an unrecognized product, an unrecognized value, and unrecognized unit, and unrecognized data field, or other error associated and the processing of the dose order. For instance in FIG. 14, an exception 962 may be provided corresponding to an error that occurred with respect to the mapping of an ingredient "Insulin" to the dose fulfillment client 140. In this regard, the exception listing 960 may include an EMR form, a substance description, a value, and a unit associated with the exception 962. Accordingly, the user may select the exception 962 and resolve the error associated therewith. For example, in FIG. 15, the dose detail screen 950 is shown such that the user has added a further ingredient 964 to the ingredient listing 820 associated with the ingredient that is the subject of the exception 962. In this regard, the user may flag the exception 962 as having been processed and made proceed with preparation of the dose by the dose fulfillment client 140.

Figure 14:
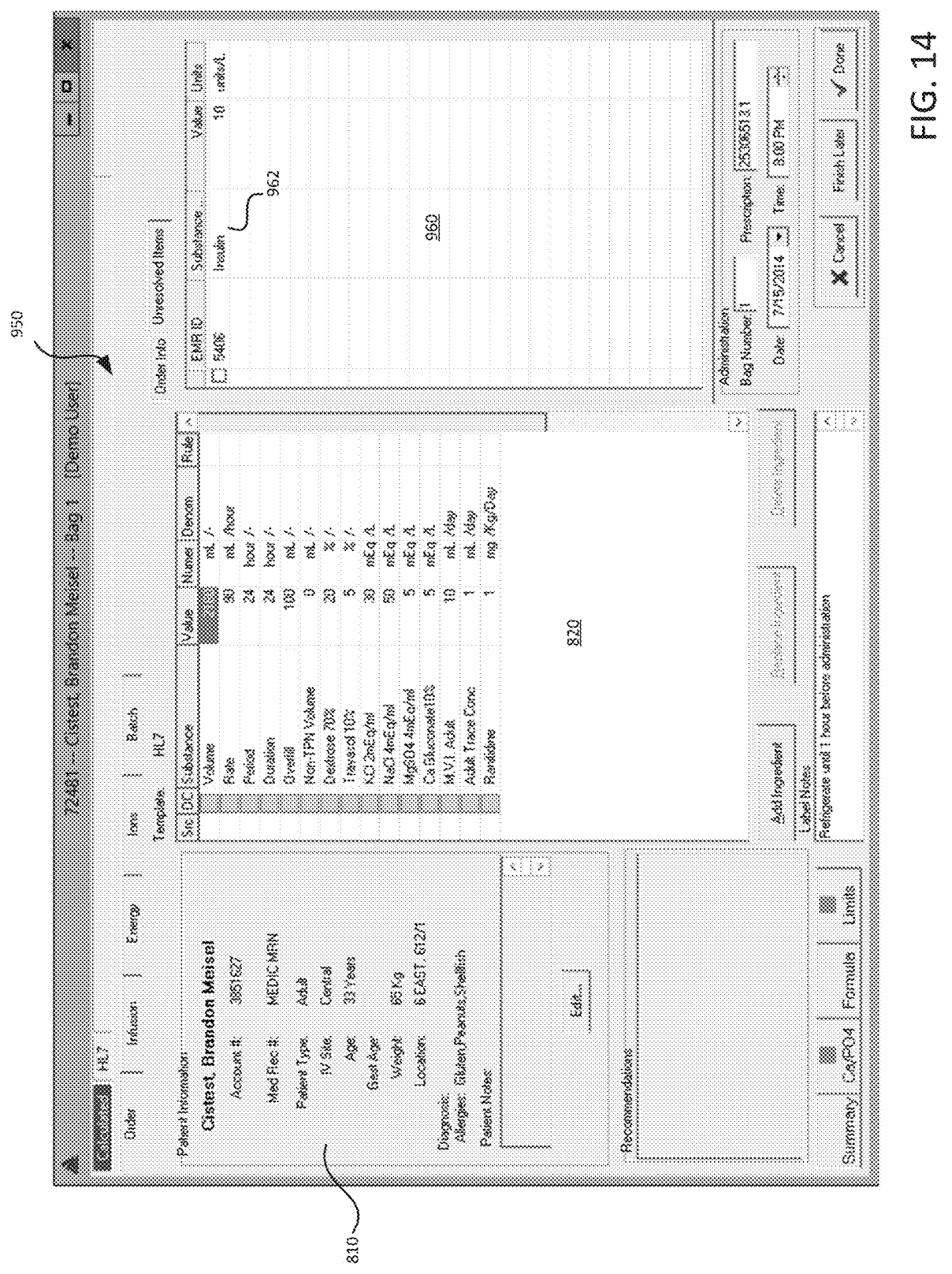
Figure 15:
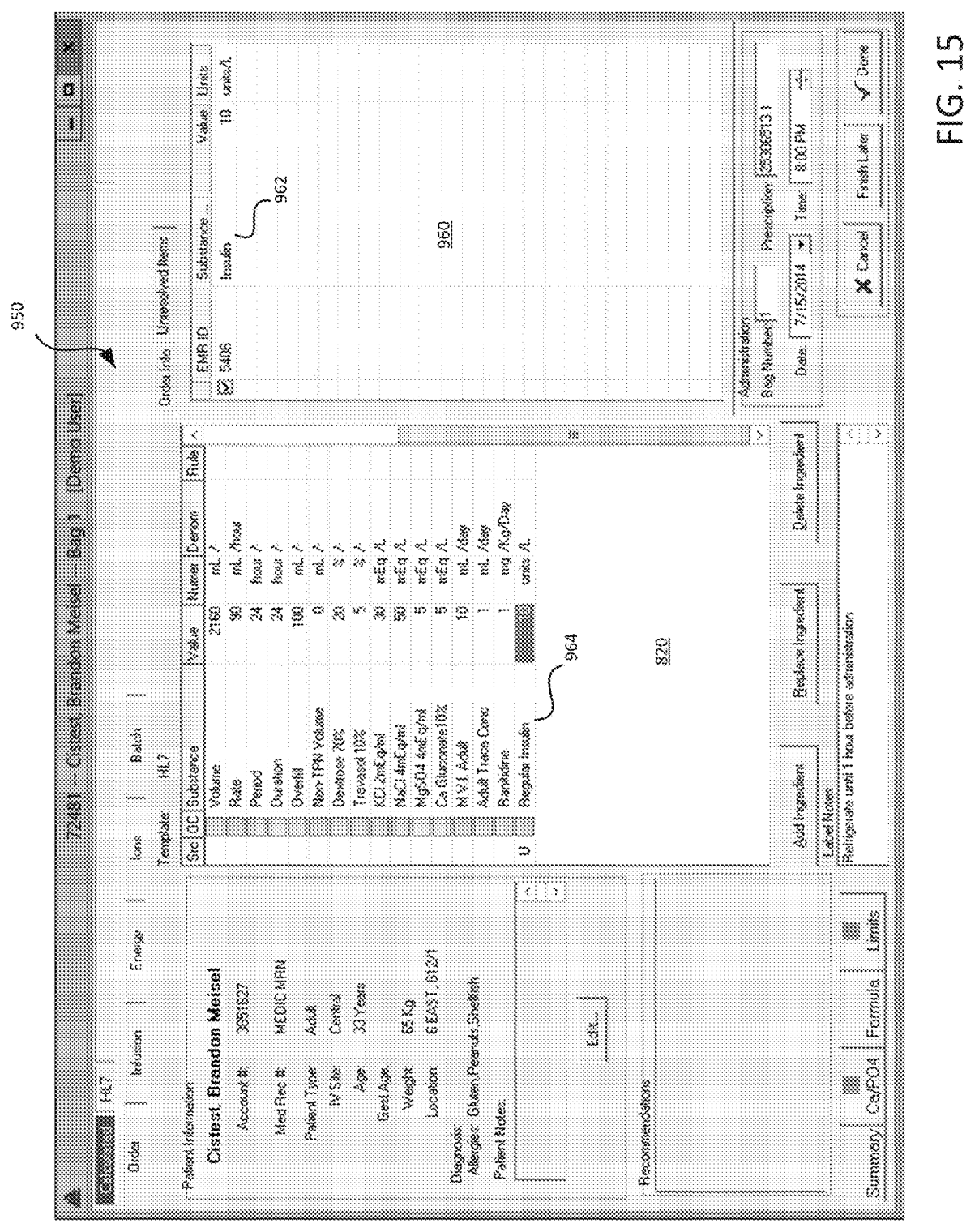
Figure 16:
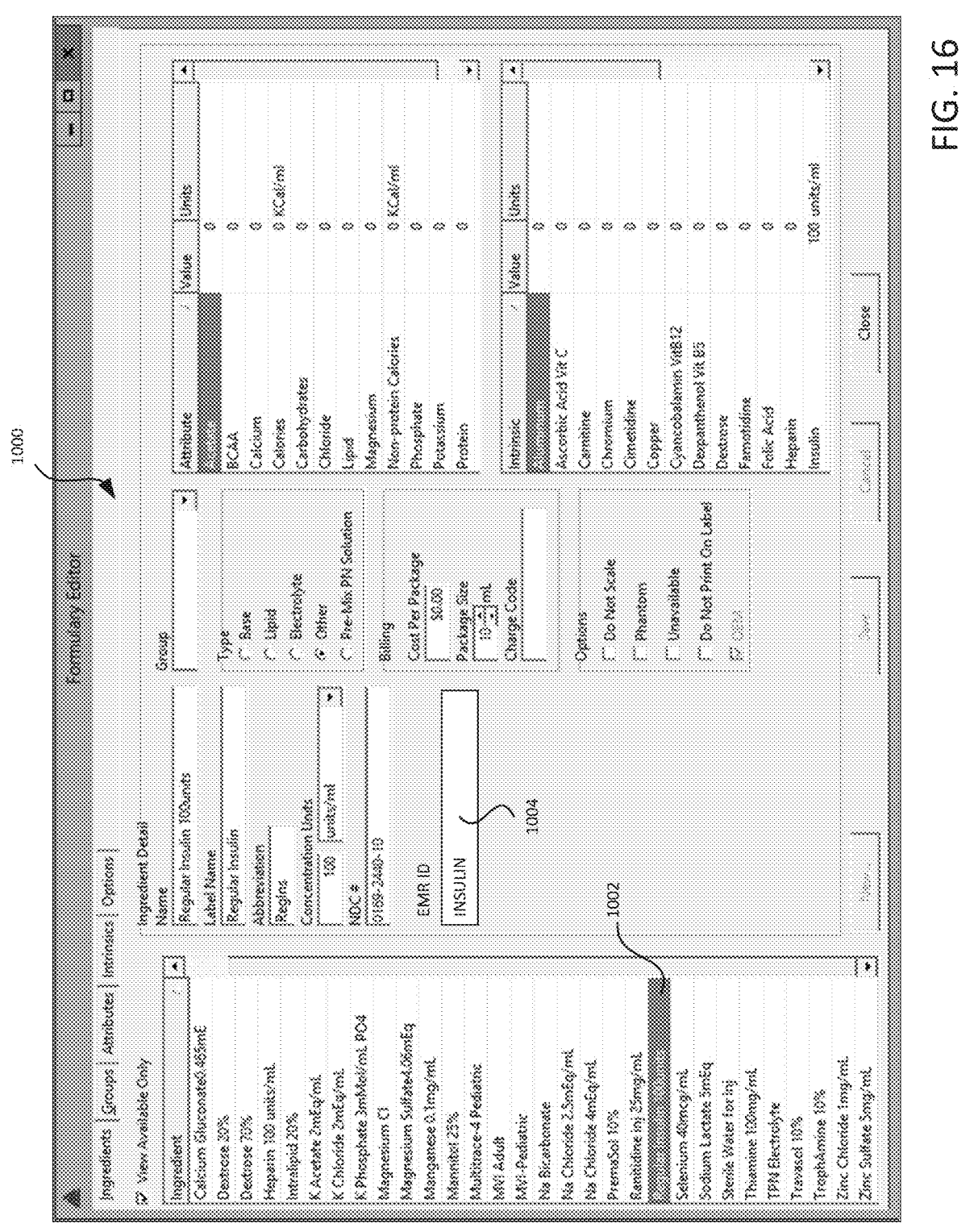

Furthermore, in FIG. 16 a user interface 1000 may be provided for use in resolution of exceptions, such as the exception 962 identified in FIGS. 14 and 15. For example, the exception 962 may be caused by an improper mapping between the EMR form for the drug "Insulin" and the client input form associated with the dose fulfillment client 140. That is, the mapping between the EMR form and the client input form may have caused an error when the platform interface module 120 and/or the transformation module 130A to process the data field containing the data related to insulin for this dose order. In this regard, the user interface 1000 may allow user to select the product 1002 for modification by the user interface 1000. In turn, the user may be operative to modify the formulary record for the selected product 1002.

Specifically, the user interface 1000 may also include a EMR correspondence field 1004 that may be used to provide the corresponding EMR form for the product 1002 at the dose fulfillment client 140. In this regard, the user may use the user interface 1000 to rectify the error in mapping between the EMR form and the client form for the drug "insulin". In turn, upon further processing of the subsequent dose order containing the ingredient "insulin", the appropriate translation may be provided such that the exception 962 may not occur in a subsequent order having the same product 1002 provided therewith. While the user interface 1000 provides for exception resolution at the dose fulfillment client 140, the exception may also be flagged at the platform interface module 120 and/or the transformation module 130 in appropriate user interfaces that may be provided to facilitate provision of a correct mapping and/or translation for a product in a dose order in a manner similar is that discussed with respect to FIG. 16. That is, the exception processing described in relation to FIG. 16 from the perspective of the dose fulfillment client 140 may also be provided in connection with the platform interface module 120 and/or transformation module 130. Furthermore, while ingredient specific processing may be fulfilled using the user interface 1000, bulk changes to the mapping between EMR forms 1730 and client forms 1720 may be facilitated by the user interface 1700 described above in connection with FIG. 17.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method for an automated exchange of healthcare information between an electronic medical record (EMR) system and a selected dose fulfillment client for fulfillment of a dose order, the method comprising:
   executing non-transitory machine-readable data for specifically configuring processors of a platform interface module, a transformation module, and a client router, execution of the non-transitory machine-readable data causing the processors to:
      receive a healthcare information data stream at the platform interface module via a network from the EMR system, wherein the healthcare information data stream comprises information including dose order metadata related to dose orders that is provided in a Health Level 7 ("HL7") format;
      identify, via the platform interface module, individual dose orders from the healthcare information data stream by identifying express delineators within the healthcare information data stream and identifying the dose order metadata corresponding to dose order data fields, wherein the express delineators mark separations between the dose orders in the healthcare information data stream;
      parse, via the platform interface module, the dose order metadata for each of the dose orders from the healthcare information data stream, wherein the dose order metadata comprises one or more dose characteristics associated with the respective dose order;
      populate, via the platform interface module, a staging table with the dose order metadata for each of the dose orders, wherein the staging table comprises a plurality of dose order data fields populated with corresponding respective portions of the dose order metadata parsed from the healthcare information data stream, and wherein the dose order metadata is populated in a standardized intermediate format;
      determine, via the transformation module from the dose order metadata, a dose fulfillment client type, among a plurality of different dose fulfillment client types for fulfilling each of the dose orders, the dose fulfillment client types including an automated dose preparation device, an automated total parenteral nutrition (TPN) compounder, and an automated dose dispensing cabinet;
      select, via the transformation module, a dose fulfillment client that matches the dose fulfillment client type for fulfillment of each of the dose orders;
      transform, via the transformation module, the dose order metadata from the standardized intermediate format into a predefined format dictated by the selected dose fulfillment client to generate transformed dose order metadata,
      wherein the transforming is at least in part based on the respective predefined format of the selected dose fulfillment client, and
      wherein the transforming includes mapping the plurality of dose order data fields of the staging table to corresponding respective ones of a plurality of dose fulfillment client input fields for the selected dose fulfillment client, including at least:
         mapping one data field of the plurality of dose order data fields of the staging table to one data field of the plurality of dose fulfillment client input fields, and
         mapping at least two data fields of the plurality of dose order data fields of the staging table to one data field of the plurality of dose fulfillment client input fields;
      route, via the client router of the transformation module, the transformed dose order metadata to the selected dose fulfillment client via the network; and
      cause each of the dose orders to be fulfilled automatically using the selected dose fulfillment client based on the transformed dose order metadata to provide a corresponding medication dose.

2. The method of claim 1, further comprising:
   receiving a first dose order in a first EMR form; and
   receiving a second dose order in a second EMR from,
   wherein the first dose order and the second dose order correspond to a dose order with identical constituent ingredients,
   wherein a form of the constituent ingredients in the first EMR form differs from the second EMR form, and
   wherein a form of the constituent ingredients for the first dose order is identical to a form of the constituent ingredients for the second dose order in the respective staging tables corresponding to the first dose order and the second dose order.

3. The method of claim 1, wherein the staging table is independent of any of the plurality of dose fulfillment clients.

4. The method of claim 1, wherein the dose fulfillment client input fields are defined by a unique input format associated with the dose fulfillment client.

5. The method of claim 4, wherein the transforming comprises:
   validating the dose order metadata of the plurality of dose order data fields with respect to the unique input format for corresponding ones of the dose fulfillment client input fields.

6. The method of claim 5, wherein the validating comprises:
   correlating the dose order metadata of the plurality of dose order data fields to formulary records of the dose fulfillment client with respect to the corresponding respective ones of the dose fulfillment client input fields.

7. The method of claim 6, further comprising:
generating an exception in response to an error associated with at least one of the mapping or validating.

8. The method of claim 7, wherein the exception comprises prompting a human user to resolve the error.

9. The method of claim 8, further comprising:
receiving, from the human user, an input associated with the resolution of the error, wherein the input comprises at least one of a correct mapping between a dose order data field of the staging table and a corresponding respective one of a dose fulfillment client input fields or a correct correlation between a portion of dose order metadata and a formulary record of the dose fulfillment client.

10. The method of claim 9, further comprising:
updating at least one of a mapping logic or a correlation logic for use in the mapping and correlating, respectively, based on the input received from the human user.

11. The method of claim 1, further comprising:
updating the staging table to indicate the dose order metadata for each of the dose orders that have been routed to the dose fulfillment client.

12. The method of claim 1, further comprising:
managing each of the dose orders prior to providing the dose order metadata in a second form to the dose fulfillment client.

13. The method of claim 12, wherein the managing includes providing a user interface to allow a user to perform a management function relative to each of the dose orders.

14. The method of claim 13, wherein the management function comprises at least one of modification of dose order metadata, cancellation of the dose order, organization of the dose order relative to other dose orders, or prioritization of the dose order relative to other dose orders.

15. The method of claim 1, further comprising:
performing logistical processing on each of the dose orders.

16. The method of claim 15, wherein the logistical processing comprises performing an action relative to each of the dose orders in response to receipt of an EMR system message subsequent to the receipt of the respective dose order.

17. The method of claim 16, wherein the EMR system message comprises at least one of a dose order change message or a dose order discontinuation message.

18. The method of claim 17, wherein the logistical processing comprises determining if the dose order metadata has been provided to the dose fulfillment client.

19. The method of claim 18, wherein the logistical processing comprises performing an action relative to each of the dose orders corresponding to the EMR system message for a dose order that has not yet been provided to the dose fulfillment client.

20. The method of claim 19, wherein the logistical processing comprises providing data to the dose fulfillment client related to the EMR system message for a dose order that has been provided to the dose fulfillment client.

21. The method of claim 20, wherein the data provided to the dose fulfillment client related to the EMR system message is transformed into a form corresponding to the dose fulfillment client.

22. The method of claim 1, further comprising:
logging activity taken with respect to each of the dose orders to generate a log regarding activities relative to the respective dose order.

23. The method of claim 22, wherein the logging comprises aggregating a plurality of logs generated relative to different respective actions taken with respect to the respective dose order.

24. The method of claim 1, wherein the healthcare information data stream is received from the EMR system.

25. The method of claim 24, wherein the EMR system comprises a hospital information system (HIS).

* * * * *